US010143782B2

(12) United States Patent
Yurek et al.

(10) Patent No.: US 10,143,782 B2
(45) Date of Patent: Dec. 4, 2018

(54) BLOOD COLLECTION CANISTER ASSEMBLY

(71) Applicant: Ecomed Solutions LLC, Mundelein, IL (US)

(72) Inventors: David A. Yurek, Mundelein, IL (US); James R. Trickett, Euclid, OH (US)

(73) Assignee: ECOMED SOLUTIONS, LLC, Mundelein, IL (US)

( * ) Notice: Subject to any disclaimer, the term of this patent is extended or adjusted under 35 U.S.C. 154(b) by 0 days.

(21) Appl. No.: 15/740,749

(22) PCT Filed: Jun. 30, 2016

(86) PCT No.: PCT/US2016/040550
§ 371 (c)(1),
(2) Date: Dec. 28, 2017

(87) PCT Pub. No.: WO2017/004449
PCT Pub. Date: Jan. 5, 2017

(65) Prior Publication Data
US 2018/0185555 A1    Jul. 5, 2018

Related U.S. Application Data

(60) Provisional application No. 62/186,604, filed on Jun. 30, 2015.

(51) Int. Cl.
*A61M 1/00* (2006.01)
*A61M 1/02* (2006.01)
(Continued)

(52) U.S. Cl.
CPC ........ *A61M 1/0007* (2014.02); *A61M 1/0017* (2014.02); *A61M 1/0052* (2014.02);
(Continued)

(58) Field of Classification Search
CPC .. A61M 1/007; A61M 1/0001; A61M 1/0017; A61M 1/0052; A61M 1/0056; A61M 1/02; A61M 1/3627
See application file for complete search history.

(56) References Cited

U.S. PATENT DOCUMENTS 3,680,560 A    8/1972  Pannier, Jr. et al.
4,346,711 A    8/1982  Agdanowski et al.
(Continued)

*Primary Examiner* — Ariana Zimbouski
(74) *Attorney, Agent, or Firm* — Christopher J. Scott

(57) ABSTRACT

A blood collection canister assembly enables a user to collect and transfer blood and includes liner and lid assemblies. The liner assembly is formed from a flexible liner material and defines an inner liner space. The lid assembly includes a primary lid portion attached to an upper mouth of the liner assembly and includes a series of ports. The series of ports may include a vacuum port, a patient port, a transfer port, and an additive port. The vacuum port is communicable with a vacuum line for directing blood transfer from a patient via the blood collection canister assembly. The patient port receives directed blood transfer from the patient, and the transfer port transfers collected blood to a separate reservoir for further processing. The blood collection canister assembly is usable in either an upright, first configuration for collecting and transferring blood or an inverted, second configuration for transferring collected blood.

34 Claims, 37 Drawing Sheets

(51) Int. Cl.
*A61M 1/36* (2006.01)
*A61J 1/05* (2006.01)

(52) U.S. Cl.
CPC ............ *A61M 1/02* (2013.01); *A61M 1/3627* (2013.01); *A61J 1/05* (2013.01)

(56) References Cited

U.S. PATENT DOCUMENTS

| | | |
|---|---|---|
| 4,419,093 A | 12/1983 | Deaton |
| 4,430,084 A * | 2/1984 | Deaton .................. A61M 1/00 141/67 |
| 4,655,740 A | 4/1987 | Ruhland |
| 4,925,055 A | 5/1990 | Robbins, III et al. |
| 5,470,324 A | 11/1995 | Cook et al. |
| 5,588,958 A | 12/1996 | Cunningham et al. |
| 6,152,902 A | 11/2000 | Christian et al. |
| 6,652,495 B1 | 11/2003 | Walker |
| 2005/0215961 A1 | 9/2005 | Romano et al. |
| 2007/0225665 A1* | 9/2007 | Perez-Cruet .......... A61F 2/4644 604/317 |
| 2008/0219642 A1 | 9/2008 | Matloub et al. |
| 2012/0330220 A1* | 12/2012 | Hensler ............... A61M 1/0056 604/22 |
| 2013/0274648 A1 | 10/2013 | Weinberger |
| 2014/0061253 A1 | 3/2014 | Sweeton |

* cited by examiner

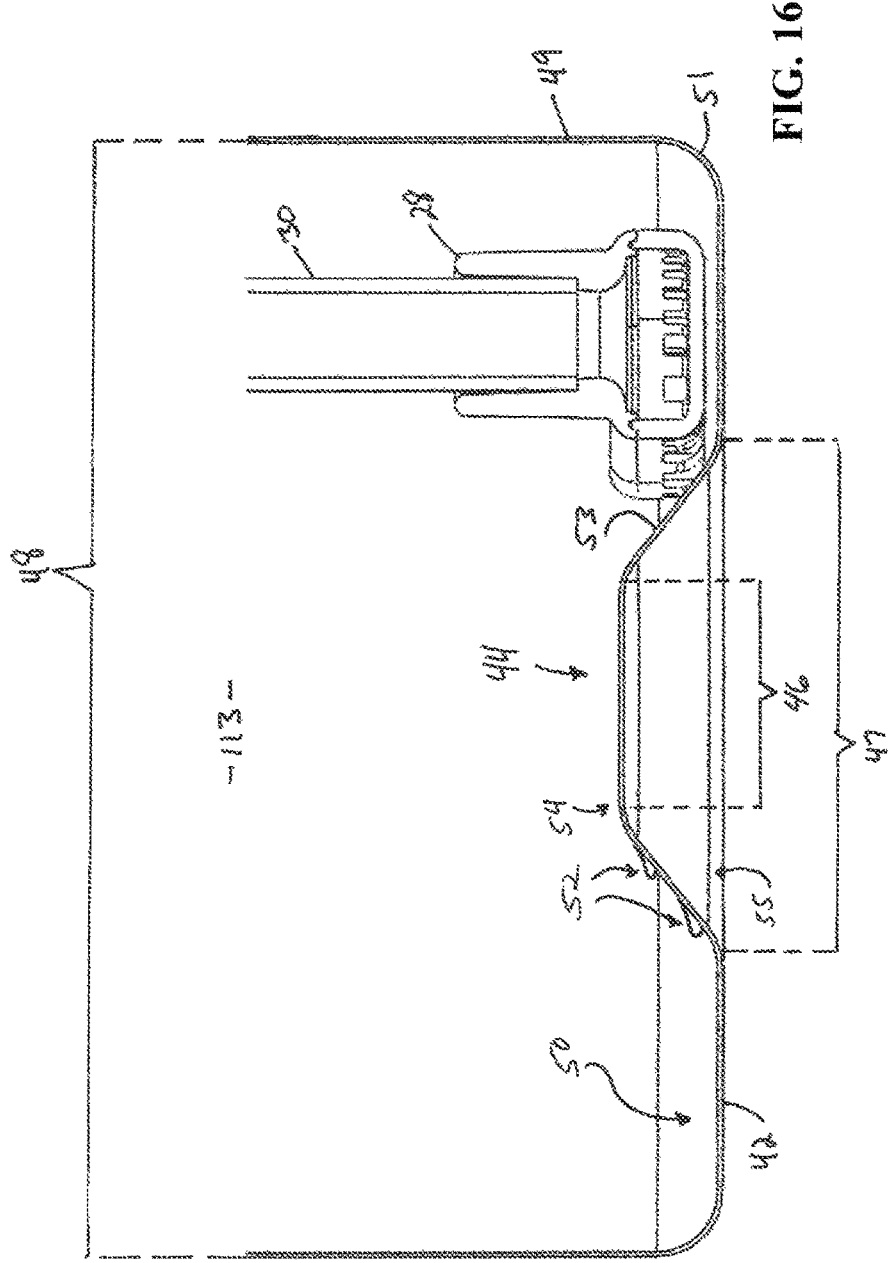

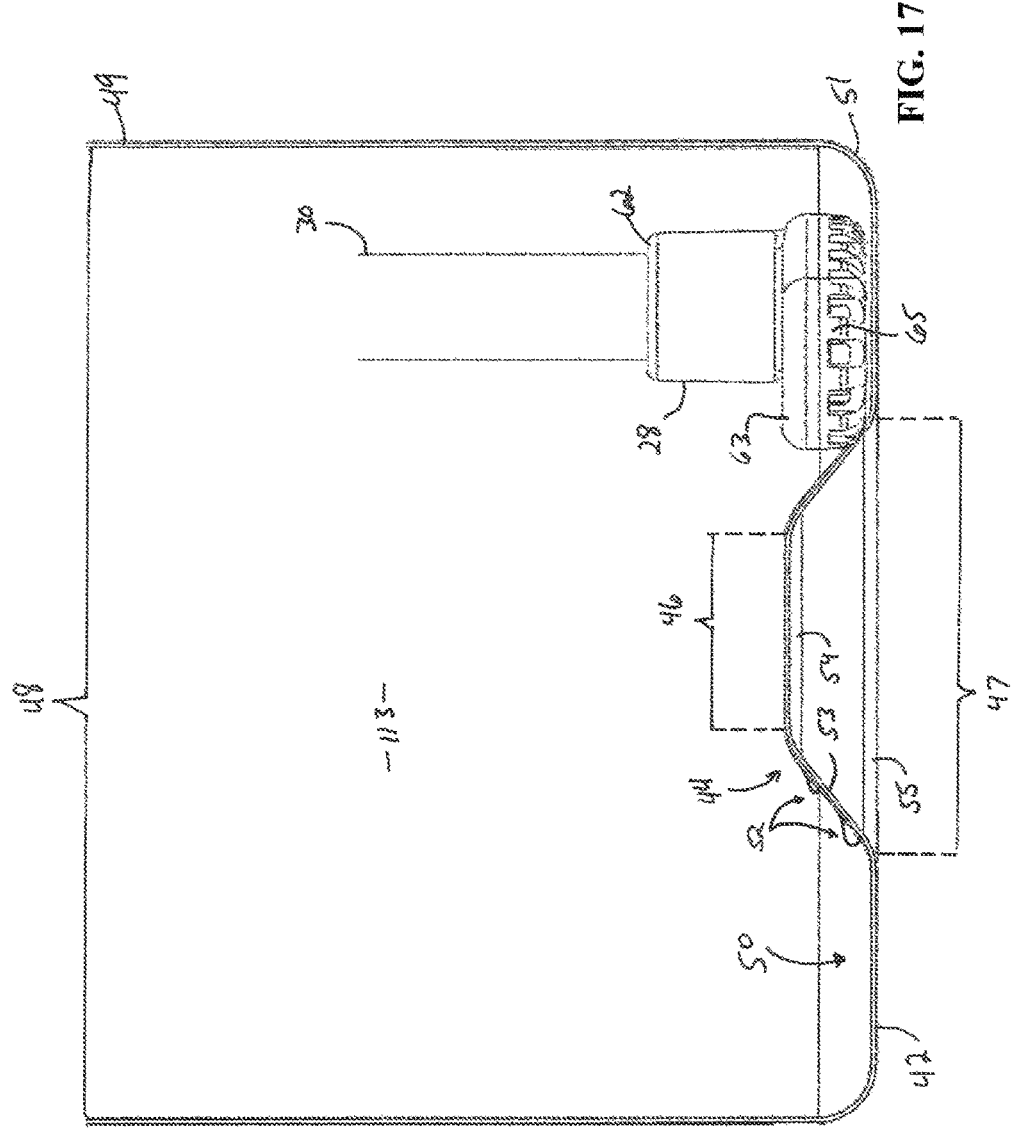

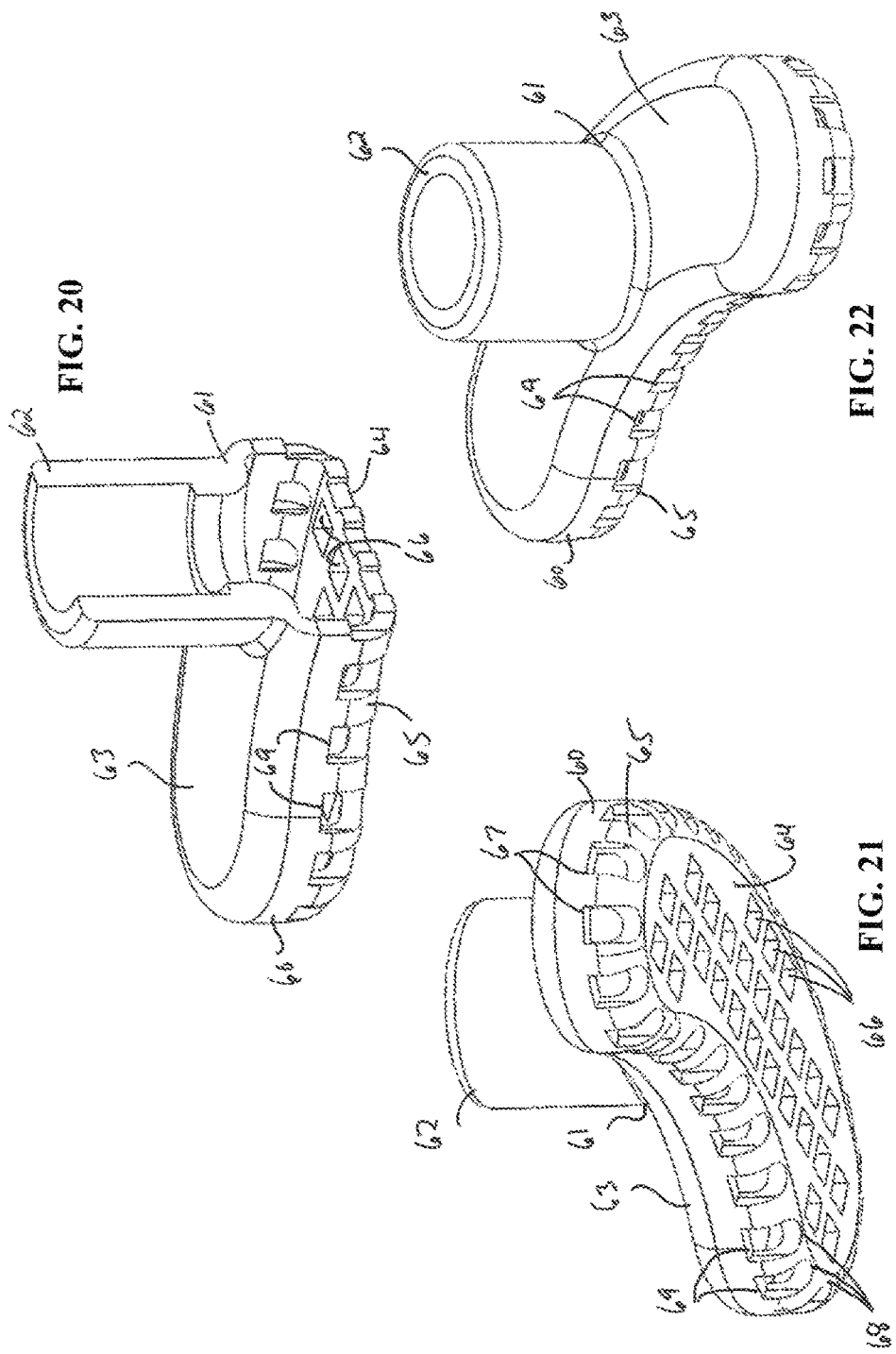

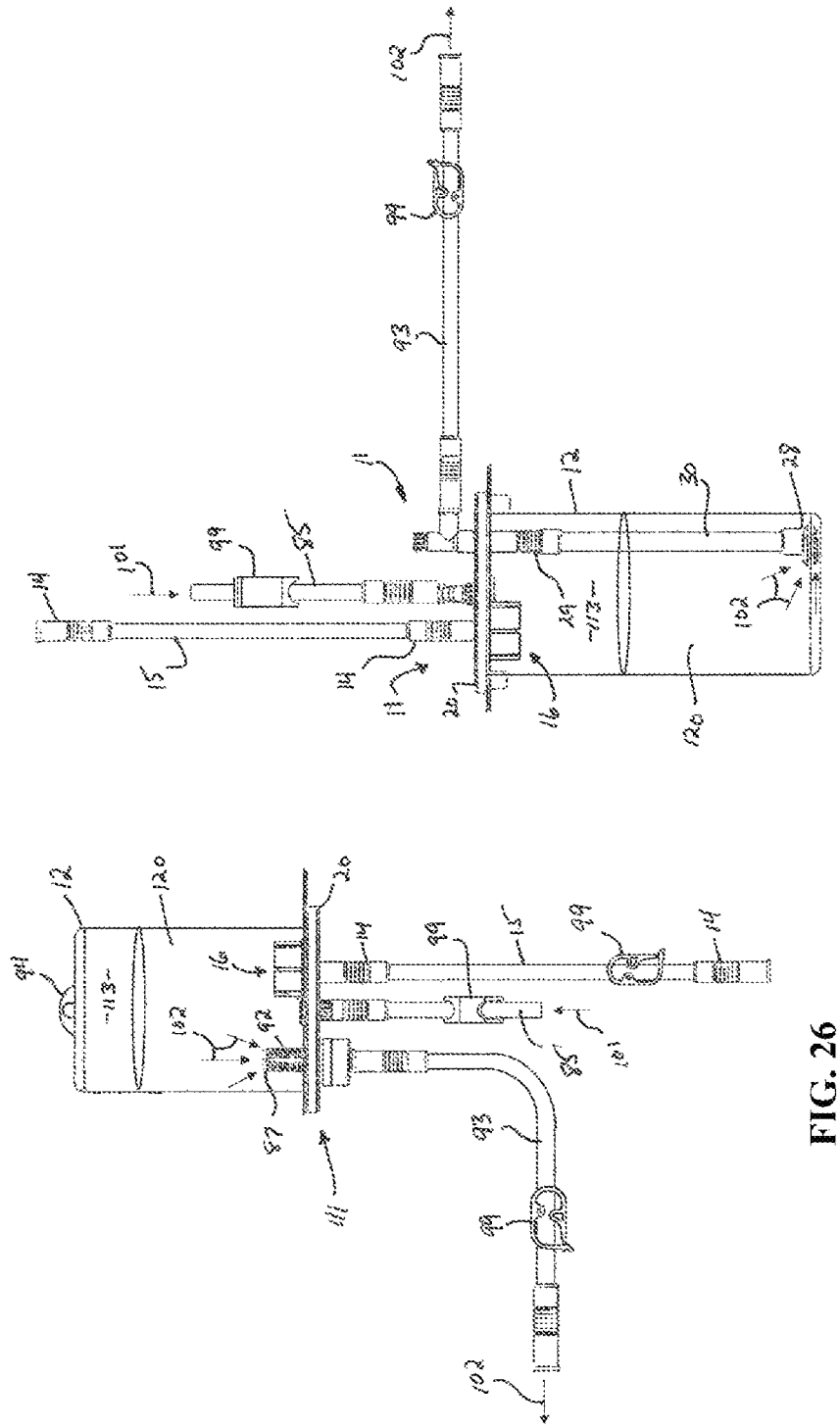

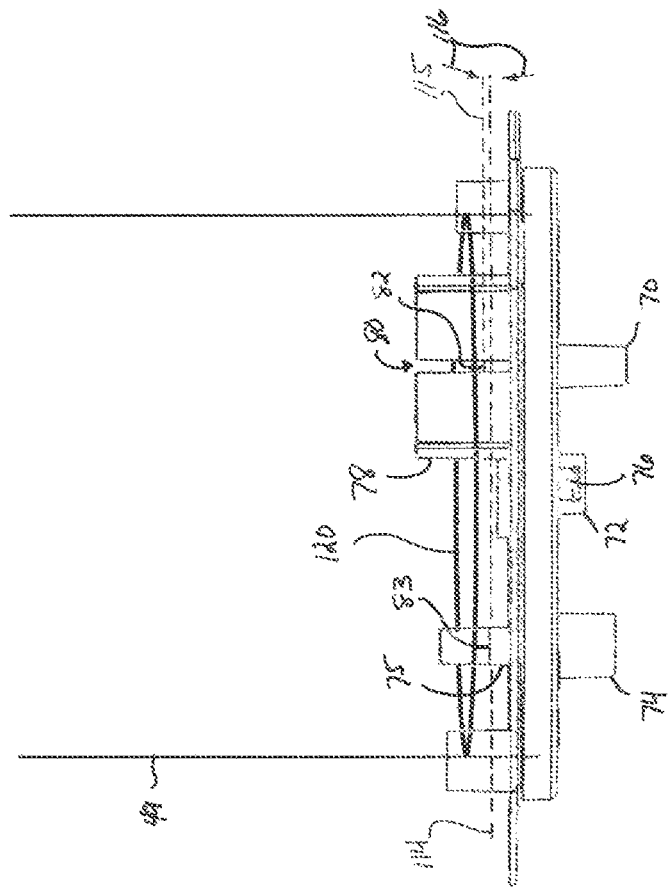

BLOOD COLLECTION CANISTER ASSEMBLY

PRIORY HISTORY

This application claims the benefit of U.S. Provisional Patent Application No. 62/186,604 filed in the United States Patent and Trademark Office on 30 Jun. 2015.

BACKGROUND OF THE INVENTION

Field of the Invention

The present invention generally relates to autologous blood collection systems and methods of blood collection for the storage, transfer and reinfusion of shed perioperative blood. More particularly, the present invention relates to a blood collection canister assembly for enabling the user to collect and transfer blood.

Brief Description of the Prior Art

Present and past devices typically only address wound drains or cardiotomy/pleural drainage and have been adapted for shed blood collection for auto-transfusion. This had led to drawbacks and increased cost association with material use and complexity for those not trained in the art of blood collection for process and/or reinfusion in the perioperative setting.

Previous liner systems have been unable to simultaneously draw and re-infuse shed blood and have been hampered by surgical fluid suction interruptions that occur when attendants are required to change out collection liners once full. The liner reservoir systems have not been ideal for various salvage set up for these reasons and trends in the industry have focused on hard shell cardiotomy reservoirs as typically used in during open heart surgery cases and adapted for use to capture shed blood. These hard shell cardiotomy systems are bulky, expensive and over-designed with many ports, water seals, and filtration parameters that require skilled personnel to set up and manage and are not economically practical to collect shed blood for evaluation to be returned to patient.

SUMMARY OF THE INVENTION

A primary advantage of the present invention is the novel use for perioperative blood collection vs. an adaptive wound drain set up or cardiotomy reservoir setup. The single use sterile liner provides sterility and decreased space use (for storage or shipping). The dip tube/filter, enables the simultaneous collection of shed blood with transfer to an auto-transfusion device for processing without having to interrupt surgical suction. The seated sterile caps enable for the additional ability to store the collected blood for transfer to a blood bank to be processed for return to the patient or direct reinfusion at any site.

The single bio-coated single lumen line enables easy set up for anyone to use by either end being compatible with the collection canister (i.e. it does not matter which end is handed off to the surgical field) along with economic advantages of a single lumen bio-coated line as distinct from complicated dual lumen aspiration and anticoagulation or AA lines. Additional color coding features further differentiate the contemplated AA line according to the present invention from surgical waste suction lines thereby maximizing viable blood being collected to sterile canister vs. waste canister/device.

The present invention is thus primarily designed to provide a novel flexible fluid collection canister assembly optionally usable in combination with a hard shell canister or housing and single lumen bio-coated aspiration and anticoagulation (AA) line. The flexible canister assembly according to the present invention basically comprises a primary lid portion attached to a flexible liner. The primary lid portion may optionally comprise or include a one-way inlet fluid port; a Luer port for administration of drugs/anticoagulant; a hook loop for hanging/storage; tethered sterile dead end caps for fluid containment; a vacuum port that is filtered and hydrophobic to maintain sterility; and a universal male/female transfer port with Luer port for sampling and clot removal.

The transfer port, in a first embodiment, is connected to a filtered dip tube assembly that is spaced from the bottom of liner to remove a maximum amount of fluid under vacuum. A specially designed filter element of the dip tube assembly removes particulate matter so as to prevent obstruction of the dip tube and transfer port. The dip tube assembly is connected specifically by a "flex" connector to the primary lid portion. This flex connector allows for the folding of the flexible liner with the dip tube element therein to enable compact storage for shipping and space requirements.

As prefaced above, in one deployment, the flexible liner may be utilized in combination with a hard shell holder and connected to vacuum. Vacuum is established via an external vacuum source and the patient port cap is designed to cam twist 45 degrees to release the port to open air to equalize pressure between liner and hard shell while maintaining sterility. The patient blood port cap can then rotate to close to allow liner to "seat" in hard shell until connected to the AA line. The AA line is delivered sterile to the operative field and either end may be passed off of the operative field to be connected to the patient port.

Measured anticoagulant may be introduced into the canister assembly via an "additive" Luer port or mixed titrated at the entry point to the canister assembly and AA line. The operative end of AA line may also be connected to a select suction wand apparatus. Shed blood/fluid may enter the AA line and bio-coating of the AA line protects blood from short term activation until the blood can be mixed via the canister reservoir or titrated at entry via the patient fluid port. The blood/fluid is collectable at the canister assembly until a determination is made to start processing with an auto-transfusion device (e.g. a Cell Saver) or for storage or disposal.

In a processing deployment, an auto-transfusion device is connected to transfer port of the blood collection canister assembly having a universal coupling for accommodating both male and female line openings to accommodate various/multiple manufacturer auto-transfusion device designs. Once a sterile connection is made, the auto-transfusion device may pull the collected blood/fluid into itself for centrifugation of shed blood/fluid and washing of red blood cell mass for later reintroduction to the patient.

In a storage deployment, the blood collection canister assembly may be capped with sterile tethered cap elements to maintain a fluid sterile barrier and may be placed on flat surface or hung from an IV pole or the like by the integral hook loop on lid. The blood collection canister assembly may thus be transported to other areas for later processing as at a point of care or by a blood bank.

In a biohazard waste disposal deployment or embodiment as in the case scenario or blood contamination or in a case of very little blood loss, the blood recovery device or collection canister assembly according to the present invention may enable canister contents removal via the transfer port for waste disposal and/or capped for biohazard disposal. A primary economic advantage of blood recovery or collection canister assembly according to the present invention is its light weight and relatively low volume for biohazard waste cost constraints.

Other features and objects of the blood recovery device or assembly according to the present invention will become more evident from a consideration of the patent drawings submitted in support of these disclosures.

BRIEF DESCRIPTION OF THE DRAWINGS

FIG. 16 is a fragmentary longitudinal cross-sectional view of bottom portions of both the liner assembly and the dip tube assembly to show the structural relationship between bottom portions of the dip tube assembly and the liner assembly.

FIG. 17 is a fragmentary longitudinal cross-sectional view of the bottom portion of the liner assembly with a fragmentary bottom portion of the dip tube assembly to show the structural relationship between bottom portions of the dip tube assembly and the liner assembly.

FIG. 20 is a vertical transverse cross-sectional top perspective view of the dip tube transfer filter element according to the present invention.

FIG. 21 is a bottom perspective view of the dip tube transfer filter element according to the present invention.

FIG. 22 is a top perspective view of the dip tube transfer filter element according to the present invention.

FIG. 26 is an additive port side depiction of a second alternative blood collection canister assembly according to the present invention shown in an inverted, second configuration for enabling blood transfer from the second alternative blood collection canister assembly shown in side-by-side relation to FIG. 27 for comparison purposes.

FIG. 27 is an additive port side depiction of the first alternative blood collection canister assembly according to the present invention shown in an upright, first configuration for enabling blood transfer from the first alternative blood collection canister assembly shown in side-by-side relation to FIG. 26 for comparison purposes.

FIG. 29 is a bottom perspective view of the vacuum filter assembly according to the present invention showing blood drainage via blood-letting slots formed in the external shroud element or structure of the vacuum filter assembly.

FIG. 30 is a fragmentary schematic depiction of portions of the second alternative lid assembly showing a container contents level inside the liner assembly and the relative elevations of a canister contents outlet and terminal slot extents of the external shroud element of the vacuum filter assembly.

DETAILED DESCRIPTION OF THE PREFERRED EMBODIMENTS

Figure 3:
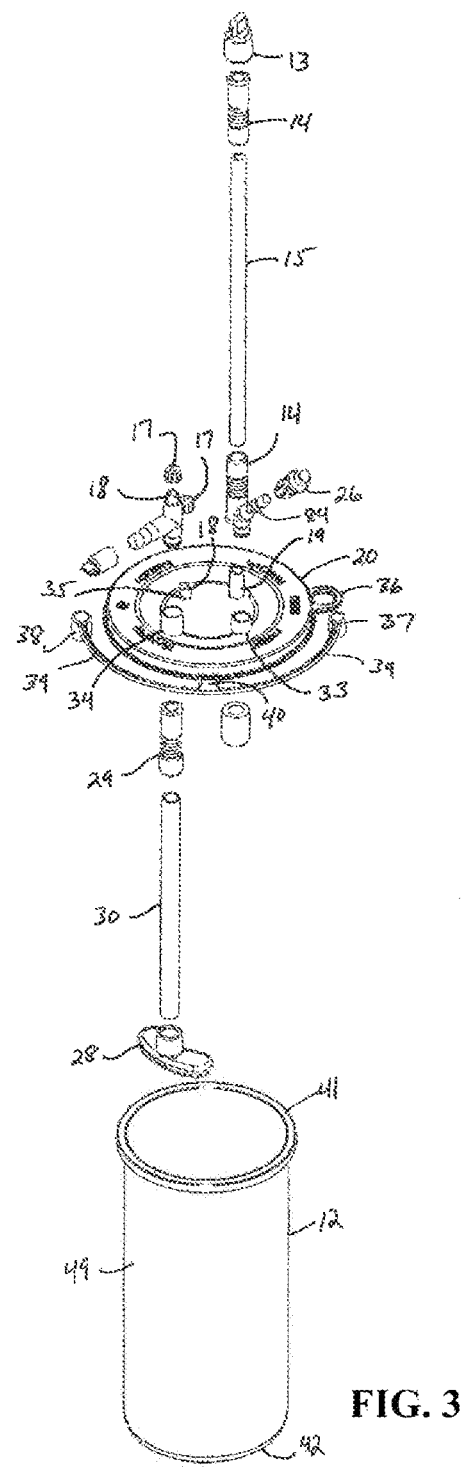
FIG. 3 is an exploded top perspective view of the first alternative lid assembly according to the present invention showing a vacuum tube assembly, a dip tube assembly, and a liner assembly exploded from the primary lid portion outfitted with a series of ports.

Referring now the drawings with more specificity, a preferred first embodiment of the present invention basically provide a novel flexible wall, fluid collection canister assembly 10 optionally usable in combination with a hard shell canister and a single lumen bio-coated Aspiration and Anticoagulant (AA) line or conduit. The flexible wall, fluid collection canister assembly 10 is generally depicted in FIG. 3 and provides a sterile, biocompatible, economical, compact, and intuitive use flexible liner canister assembly used for the collection of shed blood.

Figure 1:
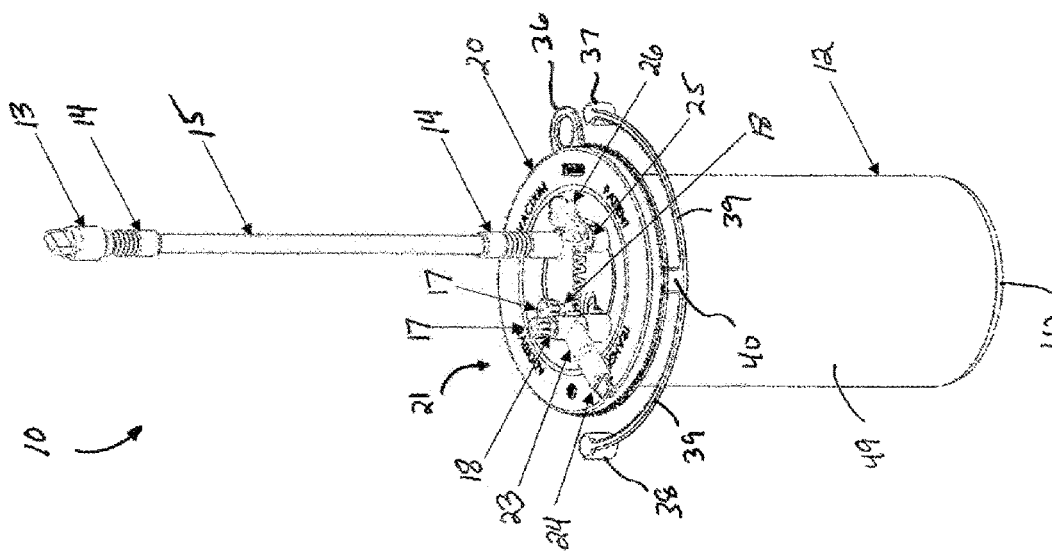
FIG. 1 is a top perspective view of a generic blood collection canister assembly according to the present invention showing an upper lid assembly and a lower liner assembly.

FIG. 1 depicts a number of components of a generic flexible wall, fluid collection canister assembly that may be said to embrace the canister assembly 10 and includes depictions of a lid assembly as at 11 and a flexible wall liner assembly as at 12. In addition to the basic components of the lid and liner assemblies 11 and 12, the canister assembly 10 more particularly comprises a number of features associated with the lid and liner assemblies 11 and 12.

These other features include a vacuum cap as at 13; vacuum flex connectors as at 14; and a vacuum tube as at 15 all of which may be said to be part of a vacuum line sub-assembly of the lid assembly 11. The vacuum line sub-assembly is preferably attached to a vacuum port 19 at external portions or an external side 21 of a primary lid portion, cover or lid element as at 20. The vacuum line sub-assembly further comprises a vacuum filter assembly 16 attached to internal portions or an internal side 22 of the primary lid portion, cover or lid element as at 20 as generally depicted and referenced in FIG. 2.

Figure 2:
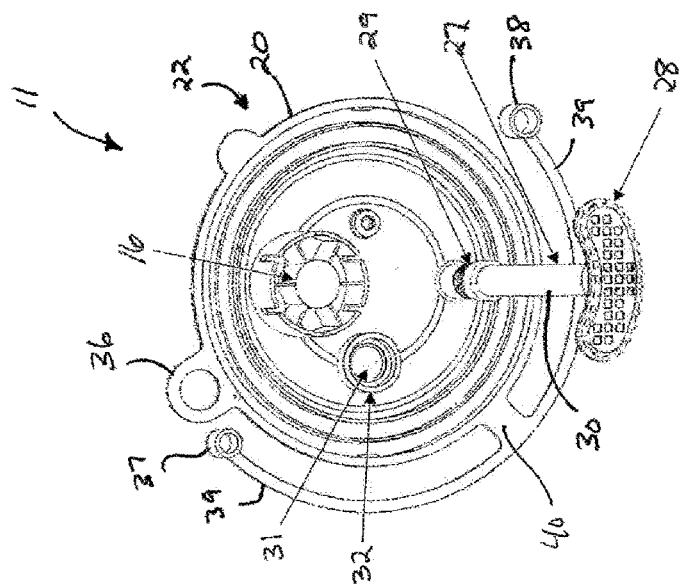
FIG. 2 is bottom perspective view of a first alternative lid assembly according to the present invention showing a dip tube assembly attached to a primary lid portion.

FIG. 1 generally depicts the external side 21 of the primary lid portion, cover or lid element 20 as attached to the flexible wall liner assembly 12, further depicts Luer lock caps as at 17; Luer lock bases as at 18; a transfer port assembly 23 having a transfer port cap 24; and a patient port assembly 25 having a patient port cap 26. FIG. 2 generally depicts the internal side 22 of the primary lid portion, cover or lid element 20 of the first alternative lid assembly 11 and thus depicts a dip tube assembly as at 27 having a lower dip tube transfer filter element as at 28, an upper dip tube flex connector as at 29, and a dip tube conduit or dip tube element as at 30. A patient port 33 formed in the primary lid portion 20 is preferably outfitted with an anti-flow flapper type valve assembly as at 31 and an anti-flow valve retainer element as at 32.

Figure 5:
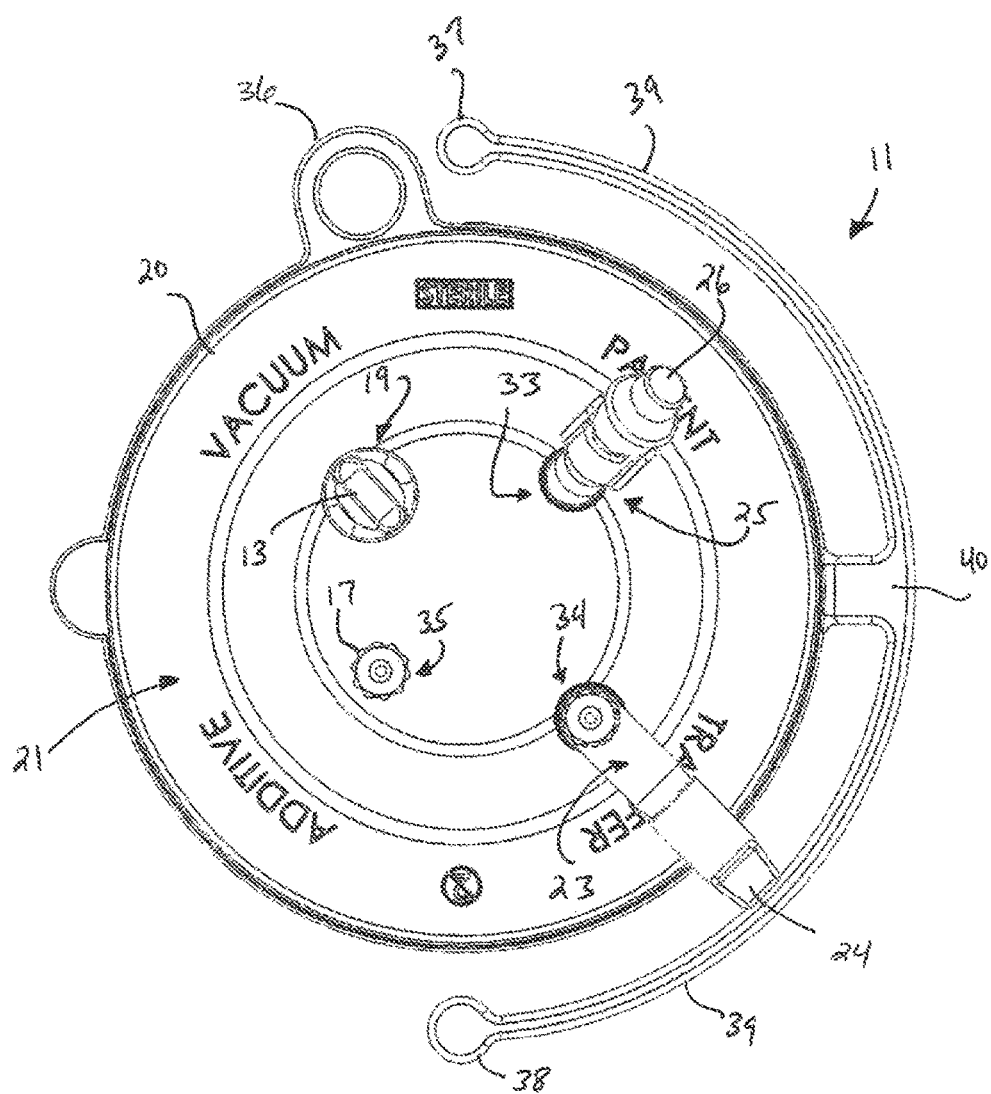
FIG. 5 is a top plan view of the first alternative lid assembly according to the present invention showing a vacuum port site, a patient port site, a transfer port site, and an additive port site.
Figure 5A:
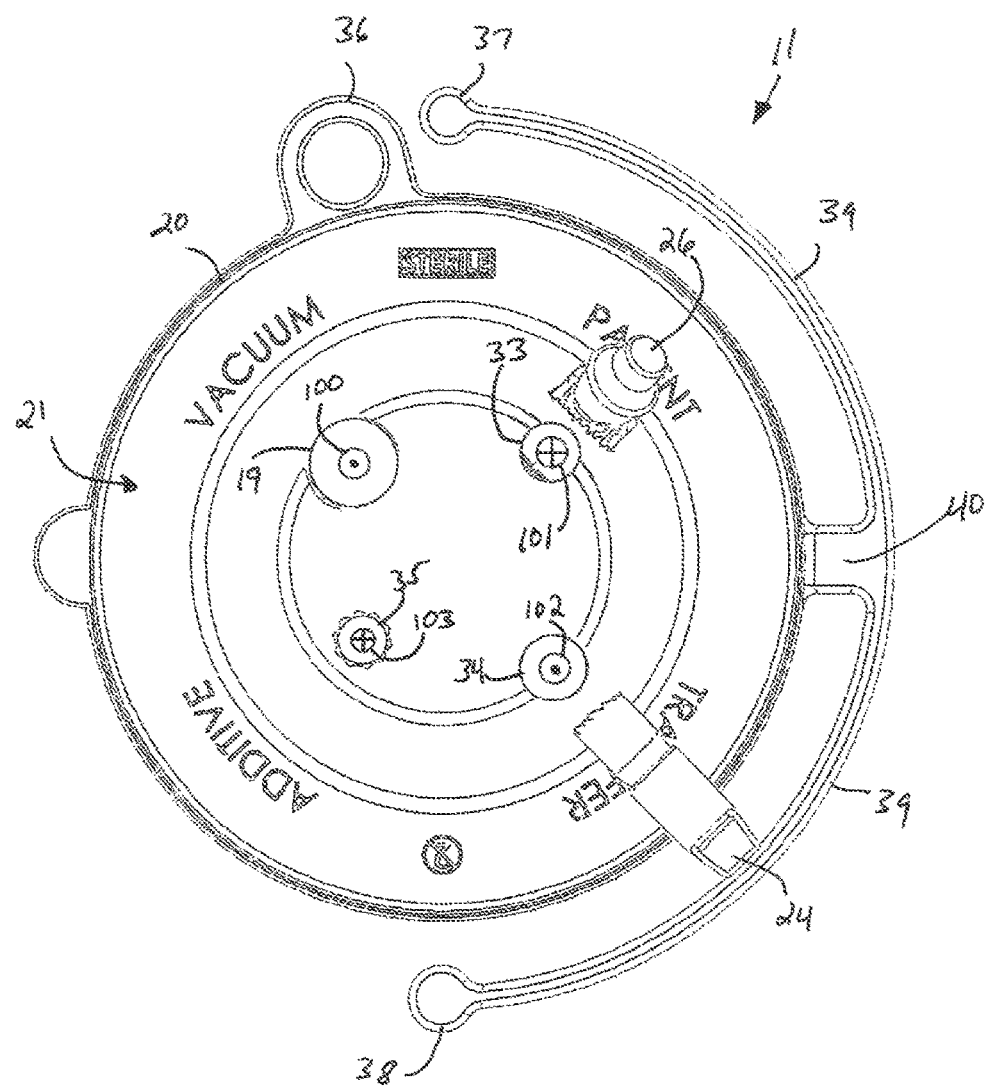
FIG. 5A is a top plan view of the first alternative lid assembly according to the present invention with parts of the vacuum port site, the patient port site, the transfer port site, and the additive port site broken away to depict vector-indicated movements of material relative to the respective port sites.

Comparatively referencing FIGS. 5 and 5A, it will thus be understood that the primary lid portion, cover or lid element 20 preferably provides a series of ports including a vacuum port as at 19, a patient port as at 33, a transfer port as at 34, and an additive port as at 35. Each of the ports 19, 33, 34, and 35 includes an external port section, an internal port section and an aperture extending therethrough. More particularly, the vacuum port 19 includes an external port section 70 and an internal port section 71; the patient port 33 includes an external port section 72 and an internal port section 73; the transfer port 34 includes an external port section 74 and an internal port section 75; and the additive port 35 includes an external port section 76 (i.e. Luer base 18) and an internal port section 77.

The vacuum port 19 operates as a force-directing or force-letting aperture via the primary lid portion 20 as at vector arrow 100 (out of the page in FIG. 5) and is communicable with an external vacuum source via a sterile line or tube element 15 to mechanically maintain a sterile connection. The tube element 15 is preferably outfitted with yellow ends and an optional yellow Roberts clamp 99 and is bonded to the primary lid portion 20 at the vacuum port 19 site. The internal port section 71 of the vacuum port 19 may preferably be outfitted with vacuum filter assembly 16. The vacuum filter assembly 16 preferably comprises or includes an external shroud element or structure 78 and an internal vacuum filter element 79.

When in the upright, first configuration (e.g. the dip tube configuration) as generally depicted in FIGS. 1, 4, 11, 12, and 27, the vacuum filter element 79 absorbs blood if canister contents 120 levels become sufficiently elevated within the inner liner space 113. If blood or container contents 120 are absorbed, the element 79 seals off the vacuum source at the internal port section 71 thereby providing a hydrophobic barrier to seal canister contents 120 from the external vacuum source and to prevent overfill. When in the second, inverted configuration otherwise referred to as the top drain configuration as generally depicted in FIGS. 26, 29, and 30, the vacuum filter element 79 readily absorbs blood and seals off the vacuum port 19 thereby providing a hydrophobic barrier while the external shroud element 78 enables blood drainage as at 81 via slot formations 80.

The slot formations 80 each have a slot terminus or maximum slot extent as at 82 that is relatively more elevated relative to an elevation of a blood inlet 83 of the internal port section 75 of the transfer port 34 when in the top drain configuration. In this regard, the elevation of the blood inlet 83 internal port section 75 of the transfer port 34 when in the top drain configuration is generally depicted at 114 and the elevation of the slot terminus or maximum slot extent 82 is generally depicted at 115 in FIG. 30. A slight offset 116 between elevation 114 and elevation 115 is thus designed into the canister assembly according to the present invention for enabling maximum blood drainage when in the top drain configuration.

The patient port 33 operates as a force-directing or force-letting aperture via the primary lid portion 20 as at vector 101 (into the page in FIG. 5A). The transfer port 34 operates as a force-directing or force-letting aperture via the primary lid portion 20 as at vector arrow 102 (out of the page in FIG. 5A) and the additive port 35 provides a inletting aperture via the primary lid portion 20 for inputting (as at vector arrow 103 into the page in FIG. 5) additives (e.g. anti-coagulant) into the inner volumetric or liner space 113 defined by the liner assembly 12 for mixing with other materials (e.g. blood) received therein.

In this last regard, the reader is further directed to FIGS. 6-9 comparatively depicting a number of assembly operating diagrams according to the present invention showing general systemic relationships inclusive of a patient as at 150 and the flexible wall, fluid collection canister assembly 10 according to the present invention with vectors 100, 101, 102, and 103 being further referenced. In this regard, vacuum airflow as at vector 100 is directed externally relative to the assembly 10 and shed blood is directed as at vector 101 externally relative to the patient 150.

Figure 6:
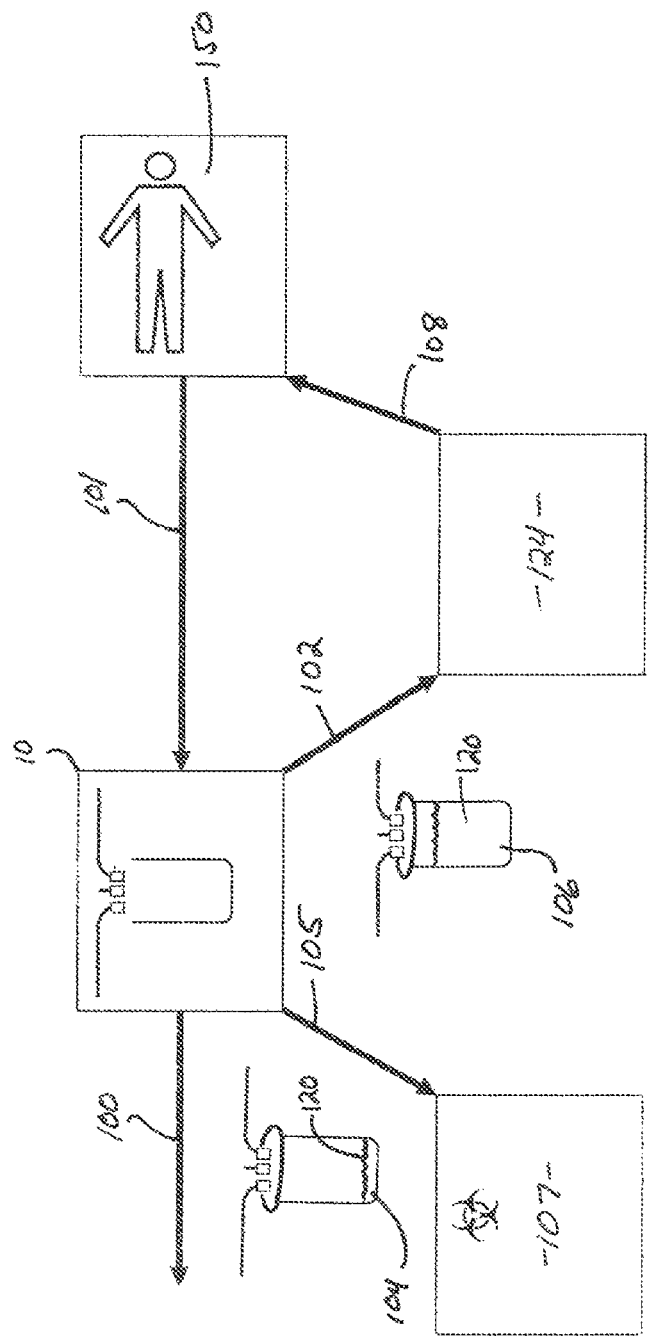
FIG. 6 is a block diagram depicting a first systemic circuit in which circuit the blood collection canister assembly according to the present invention plays a central role, and which circuit includes an external vacuum source, a patient, the blood collection canister assembly, an auto-transfusion device/system and/or an optional biohazard waste disposal.

If a relatively small volume of shed blood is collected as at 104 (i.e. an insufficient volume for processing), the disposable flexible wall, fluid collection canister assembly 10 may be sent to biohazard waste disposal 107 as at vector 105. If a relatively large volume of shed blood is collected as at 106, the shed blood volume 106, may be transferred as at arrow 102 to an auto-transfusion device or system as at 124. After intraoperative blood salvage or cell salvage or autologous blood transfusion, the processed blood may be reintroduced into the patient 150 as at vector arrow 108 all as generally depicted in FIG. 6. Alternative blood collection scenarios are generally and comparatively depicted in FIGS. 7-9.

Figure 7:
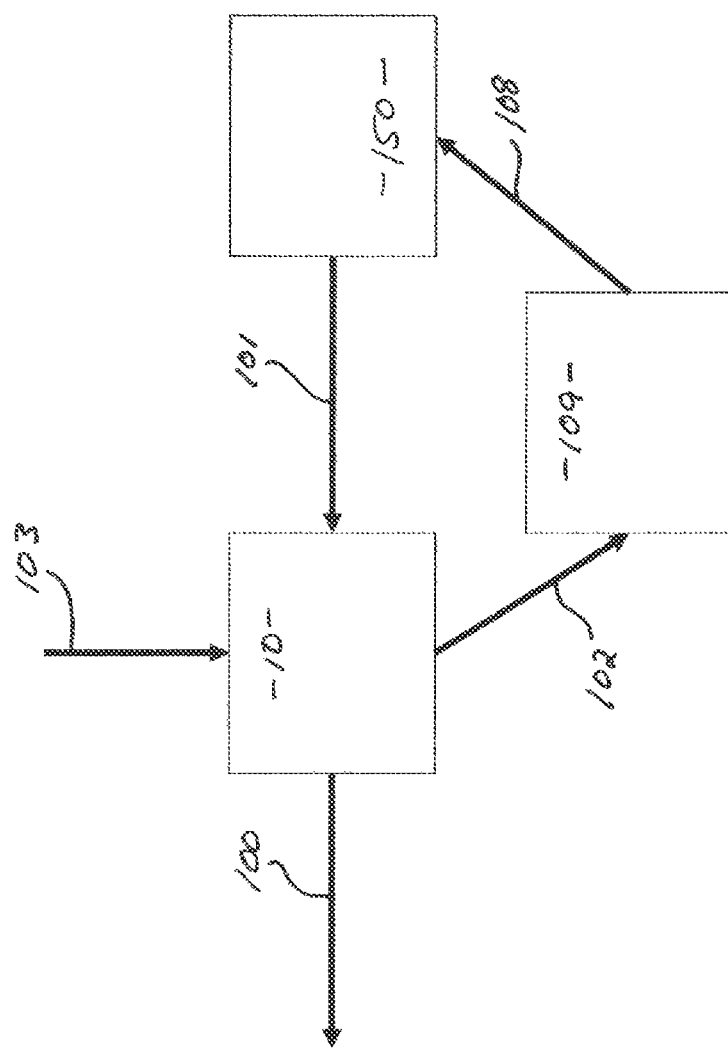
FIG. 7 is a block diagram depicting a second systemic circuit in which circuit the blood collection canister assembly according to the present invention plays a central role, and which circuit includes an external vacuum source, an external anticoagulant source, a patient, the blood collection canister assembly, and a blood bank.

FIG. 7 generally depicts a blood bank collection scenario whereby shed blood is collected as at vector 101 from a patient 150 under the direction of a vacuum vector force 100 via the flexible wall, fluid collection canister assembly 10. Anti-coagulant may be introduced as at vector 103 into the shed blood contained within the canister assembly 10 via the additive port 35 and the resulting mix may be transferred as at vector 102 to a blood bank 109. Stored blood from the blood bank 109 may be reintroduced as at vector arrow 108 into the patient 150.

Figure 8:
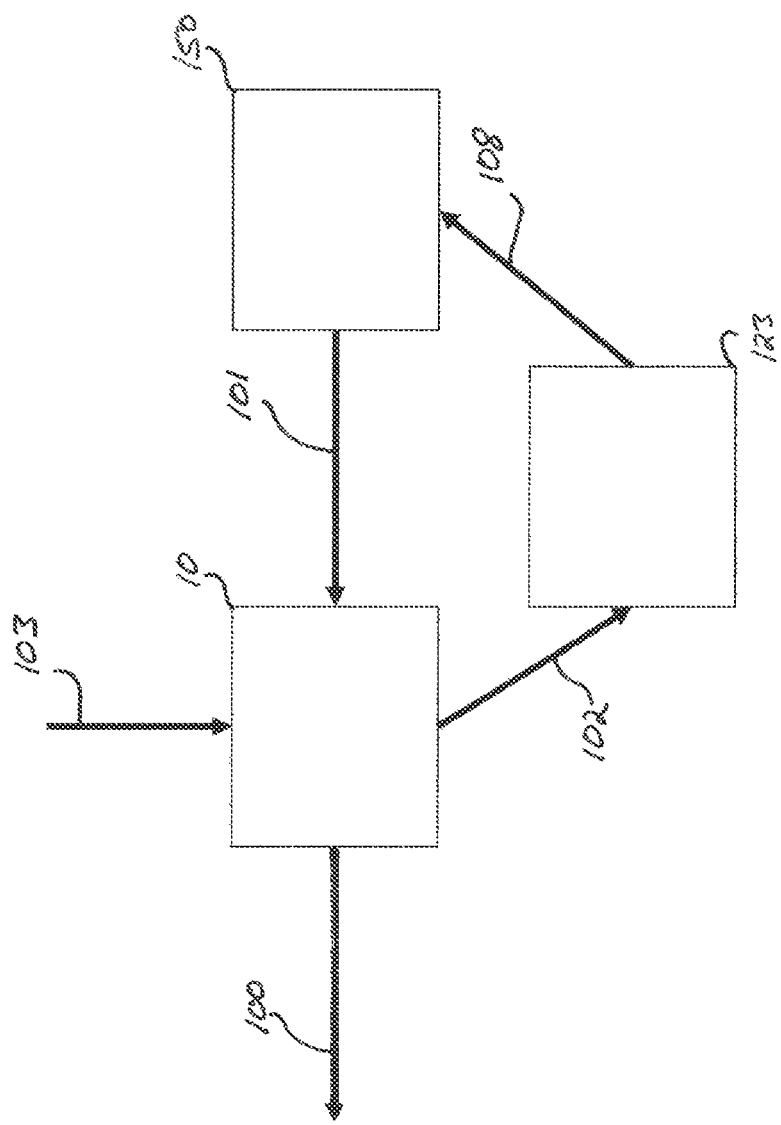
FIG. 8 is a block diagram depicting a third systemic circuit in which circuit the blood collection canister assembly according to the present invention plays a central role, and which circuit includes an external vacuum source, an external anticoagulant source, a patient, the blood collection canister assembly, and a blood bag with filter assembly.

FIG. 8 generally depicts a blood bag collection scenario whereby shed blood is collected as at vector 101 from a patient 150 under the direction of a vacuum vector force 100 via the flexible wall, fluid collection canister assembly 10. Anti-coagulant may be introduced as at vector 103 into the shed blood contained within the canister assembly 10 via the additive port 35 and the resulting mix may be transferred as at vector 102 to a blood bag with filter assembly as at 123. Stored blood from the blood bag/filter assembly 123 may be reintroduced as at vector arrow 108 into the patient 150.

Figure 9:
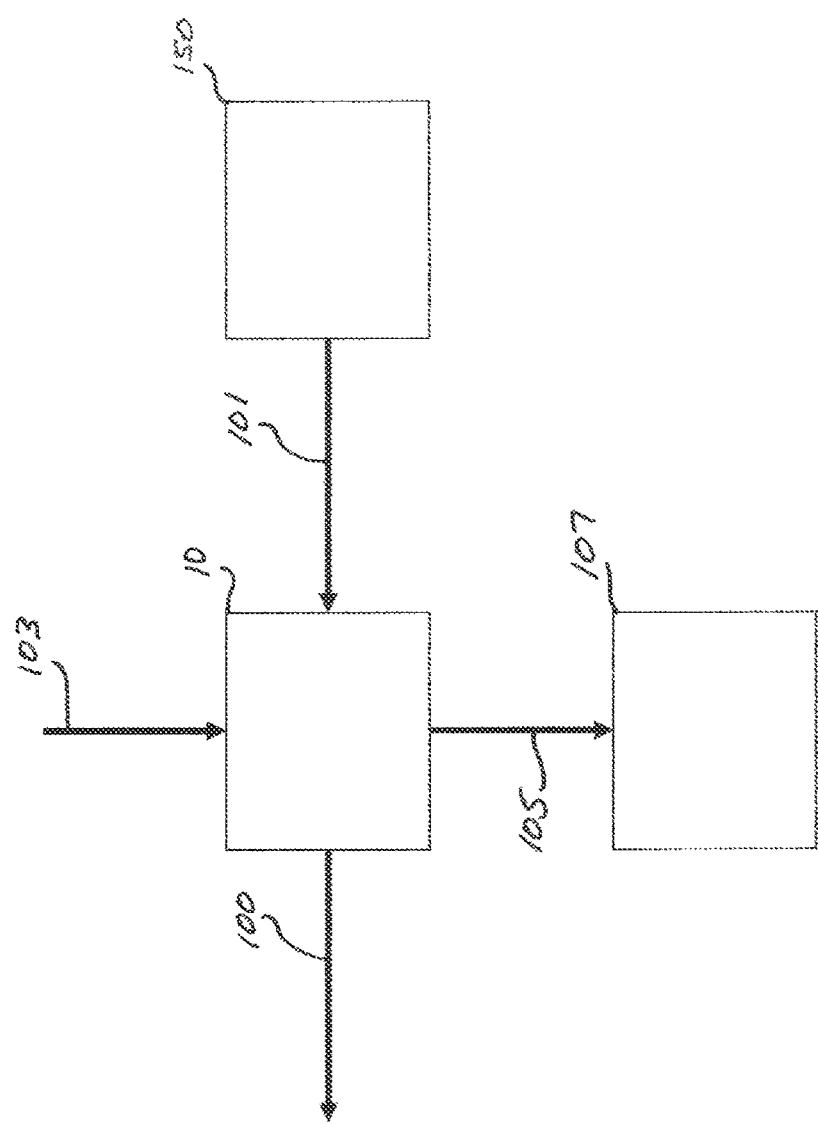
FIG. 9 is a block diagram depicting a fourth systemic circuit in which circuit the blood collection canister assembly according to the present invention plays a central role, and which circuit includes an external vacuum source, an external anticoagulant source, a patient, the blood collection canister assembly, and a biohazard waste disposal.

FIG. 9 generally depicts a simple biohazard waste disposal scenario whereby shed blood is collected as at vector 101 from a patient 150 under the direction of a vacuum vector force 100 via the flexible wall, fluid collection canister assembly 10. Anti-coagulant may be introduced as at vector 103 into the shed blood contained within the canister assembly 10 via the additive port 35. If the resulting mix is destined for disposal, the disposable flexible wall, fluid collection canister assembly 10 may be sent to biohazard disposal 107 as at vector 105.

The vacuum tube sub-assembly contemplated or embraced by the present invention preferably comprises a 0.25-inch diameter, 12-inch long vacuum tube 15 with color-coded yellow flex connectors 14 structurally located at and attached to both ends of the vacuum tube 15. The flex connector 14 attached to the vacuum port 19 may preferably be permanently bonded to the vacuum port 19 and the other free end may be preferably outfitted with a vacuum cap 13. When the vacuum cap 13 is removed, the flex connector 14 at the free end may be attached to an external vacuum source (not specifically illustrated) for imparting directive force 100 as exemplified by a vacuum airflow.

Figure 43:
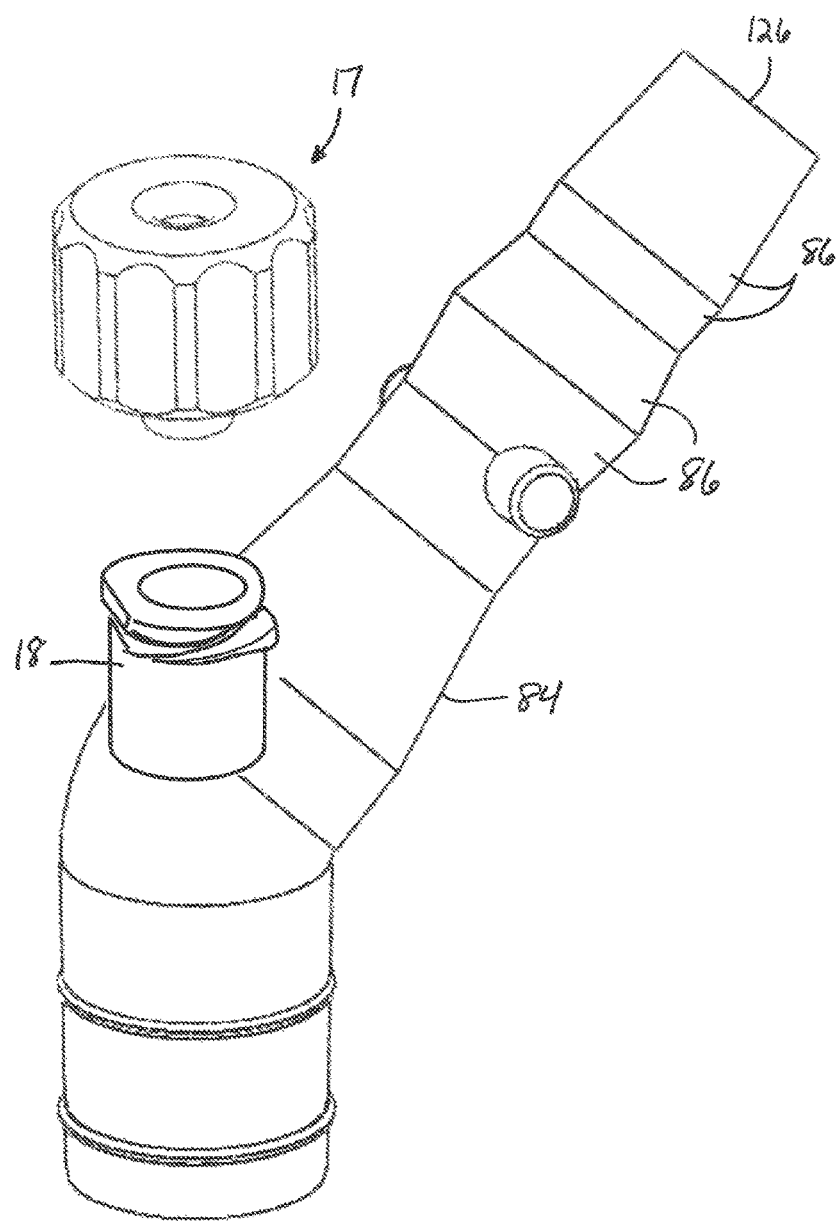
FIG. 43 is an enlarged top perspective view of a patient port elbow element outfitted with a Luer lock base and a Luer lock cap exploded from the Luer lock base.
Figure 44:
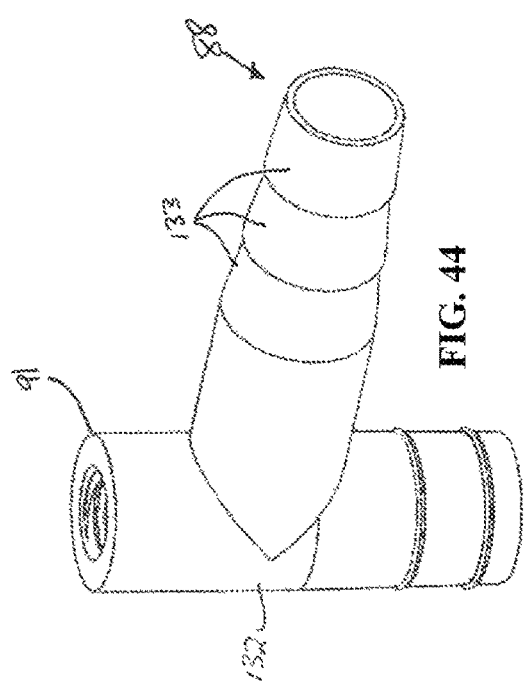
FIG. 44 is a top perspective view of a transfer port elbow element with universal coupling according to the present invention.
Figure 46:
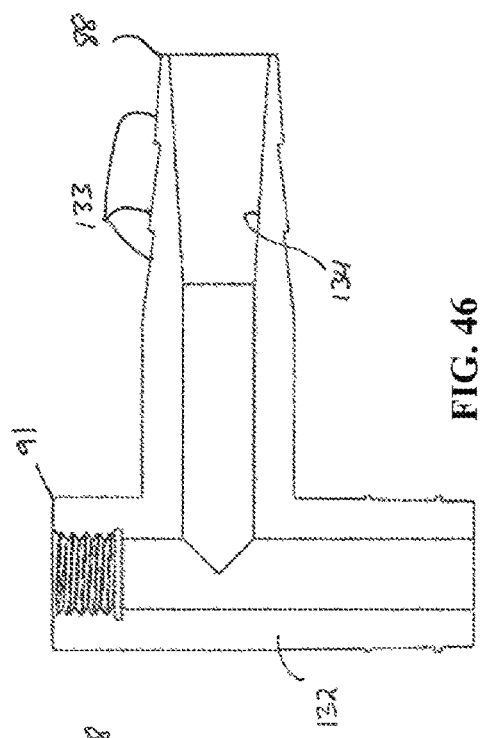
FIG. 46 is a medial cross-sectional view of the transfer port elbow element with universal coupling according to the present invention.
Figure 45:
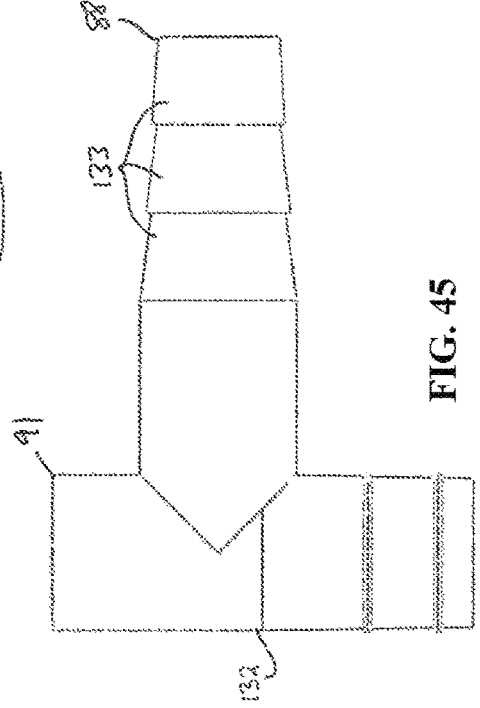
FIG. 45 is a lateral elevational view of the transfer port elbow element with universal coupling according to the present invention.
Figure 46A:
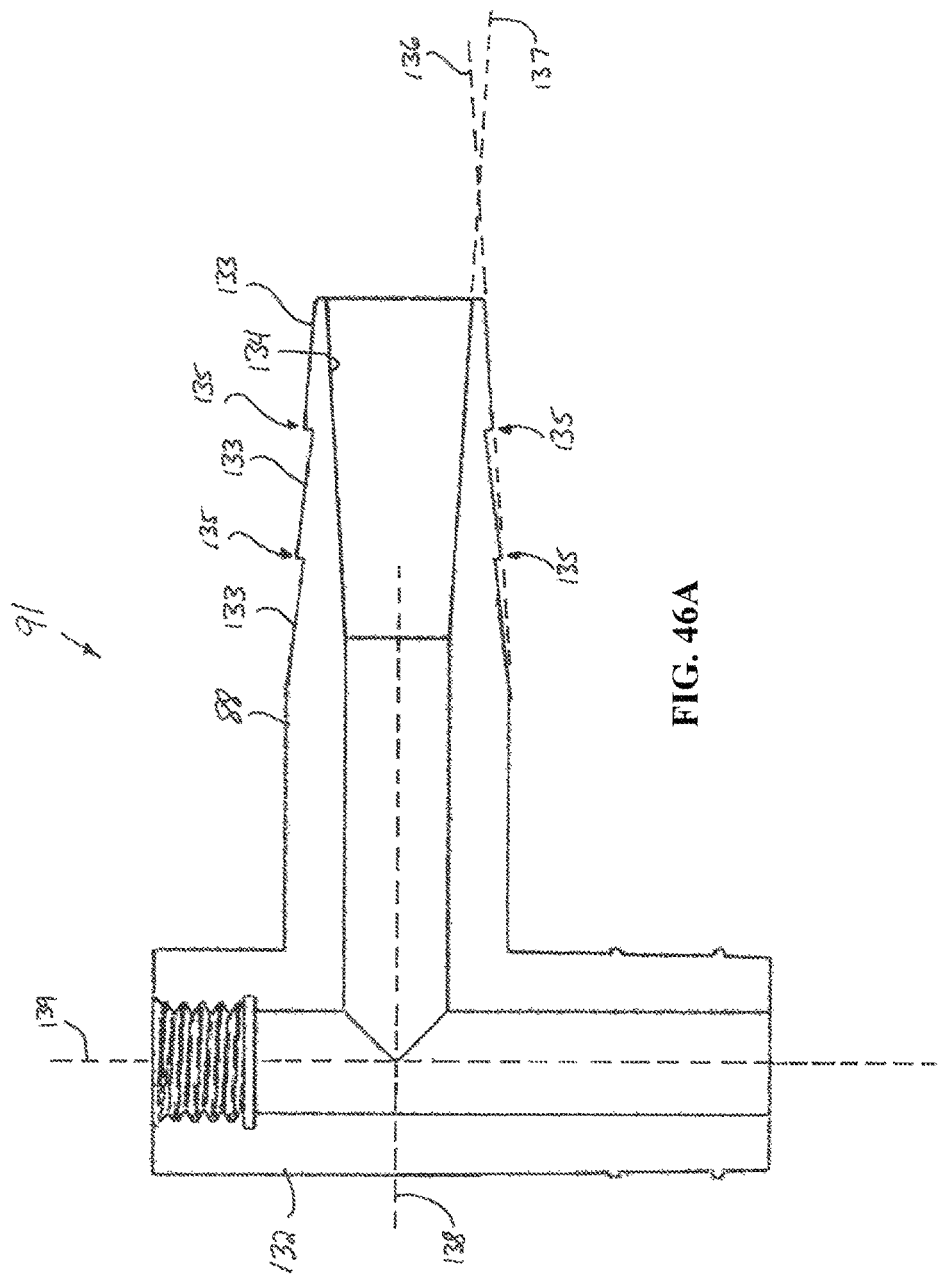
FIG. 46A is an enlarged medial cross-sectional view of the transfer port elbow element with universal coupling according to the present invention as enlarged from FIG. 46 to show in greater detail structures associated with the transfer port elbow element with universal coupling.

The patient port assembly 25 is outfitted upon the patient port 33 and is preferably made compatible with 0.25 inch blood transfer tubing 85 and outfitted with a color-coded green twist cap 26 to aid in sanitary rapid air intake during assembly setup. The blood transfer tubing 85 preferably thus comprises green color coded ends and may be outfitted with an optional green Roberts clamp 99. The patient port assembly 25 preferably further comprises a 45-degree elbow structure as at 84 for enabling enhanced blood flow and entry of the blood delivery line as exemplified by either a dual lumen line or a bio-coated single lumen line as generically depicted and referenced at 85. The patient port assembly 25 further contemplates an integrated Luer port assembly as at cap 17 and base 18 in FIG. 43 for providing a preferable point of entry or input mechanism for mixing anticoagulant with aspirated blood.

The patient port cap element as at 26 is attachable to the 45-degree elbow structure 84 and seals or enables flow of matter through the patient port 33 via the end orifice 126. The cap element 26 is preferably outfitted with certain means for maintaining novel mechanical sterile equalization of air pressure between the soft shell or soft wall liner assembly 12 and a hard shell canister usable in combination the canister assemblies according to the present invention. In this regard, it is contemplated that the cap element 26 may be rotated an intermediate number of rotational degrees (e.g. 45 rotational degrees) to allow a narrow air flow channel as at 127 between the tapered outer surfacing 86 of the patient port elbow element 84 and the inner surfacing 128 of the cap element 26 as generally and comparatively depicted in FIGS. 34-42.

In this last regard, the reader will note the tapered outer surfacing 86 of the elbow structure 84, which surfacing 86 cooperates with internal surfacing 128 of the cap element 26 to enable minimized or reduced air flow for pressure equalization between the inner liner assembly 12 and the outer hard shell canister 117. Comparing FIGS. 37-39 and FIGS. 40-42, the reader will there note respective sequential depiction of the patient port assembly in various stages of operation whereby FIGS. 37 and 40 depict the patient port cap element in a first rotative position relative to the patient port elbow element for preventing air passage through the end orifice 126 of the patient port assembly 25.

Figure 39:
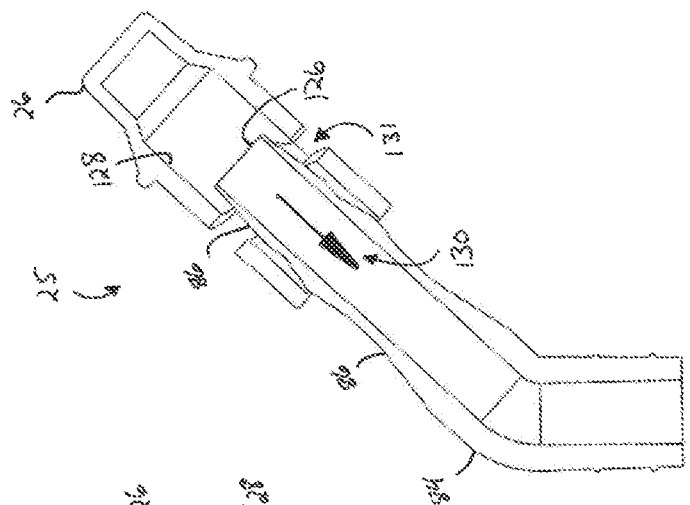
FIG. 39 is a third sequential depiction of a patient port assembly shown in longitudinal or medial cross-section with the patient port cap element being shown in a third (rotative) position relative to the patient port elbow element for enabling a relatively broad air passage intermediate the patient port cap and elbow elements, the third (rotative) position for enabling unobstructed free flow of air through the end orifice of the patient port assembly.
Figure 38:
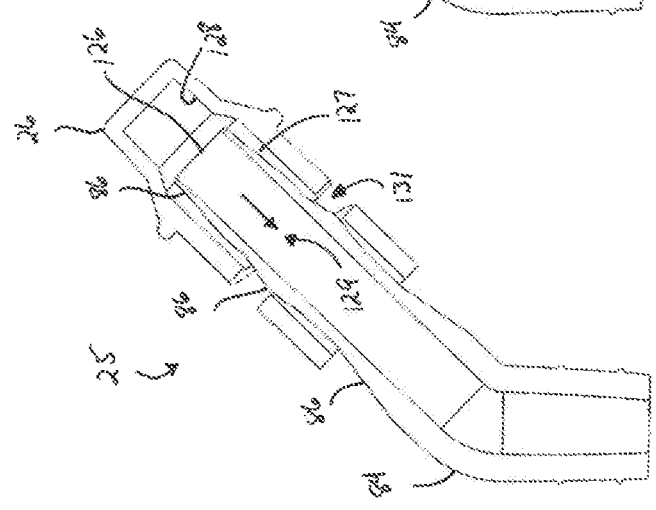
FIG. 38 is a second sequential depiction of a patient port assembly shown in longitudinal or medial cross-section with the patient port cap element being shown in a second (rotative) position relative to the patient port elbow element for enabling a relatively narrow air passage intermediate the patient port cap and elbow elements, the second (rotative) position for enabling pressure equalization between an inner liner assembly and an outer hard shell canister.
Figure 37:
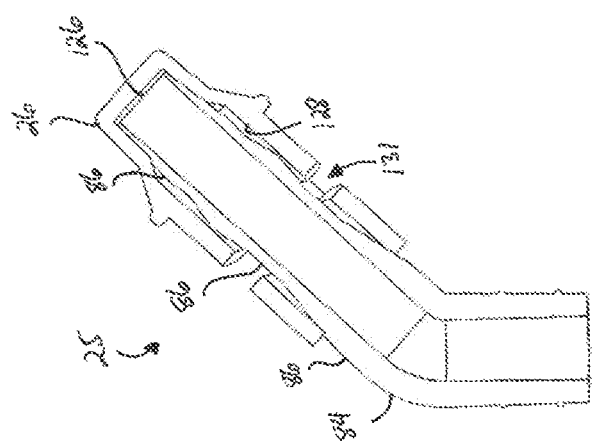
FIG. 37 is a first sequential depiction of a patient port assembly shown in longitudinal or medial cross-section with the patient port cap element being shown in a first (rotative) position relative to the patient port elbow element for preventing air passage through the end orifice of the patient port assembly.
Figure 42:
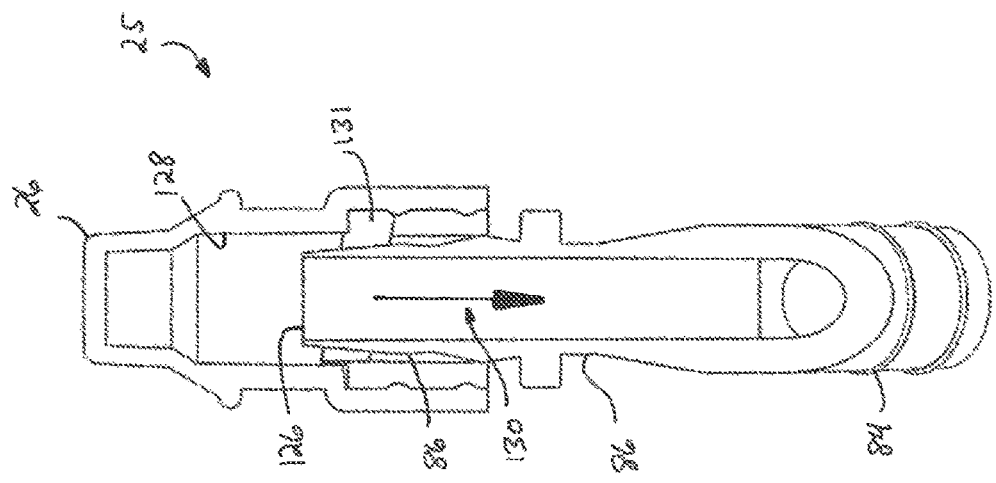
FIG. 42 is a third sequential depiction of a patient port assembly shown in latitudinal or coronal cross-section with the patient port cap element being shown in a third (rotative) position relative to the patient port elbow element for enabling a relatively broad air passage intermediate the patient port cap and elbow elements, the third (rotative) position for enabling unobstructed free flow of air through the end orifice of the patient port assembly.
Figure 41:
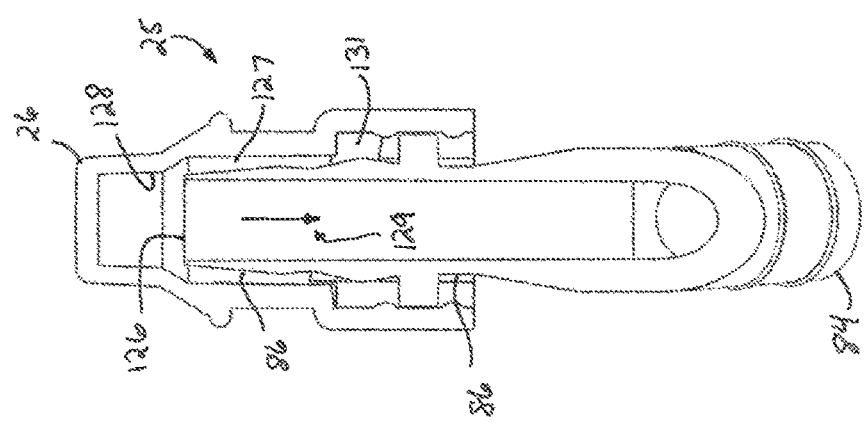
FIG. 41 is a second sequential depiction of a patient port assembly shown in latitudinal or coronal cross-section with the patient port cap element being shown in a second (rotative) position relative to the patient port elbow element for enabling a relatively narrow air passage intermediate the patient port cap and elbow elements, the second (rotative) position for enabling pressure equalization between an inner liner assembly and an outer hard shell canister.
Figure 40:
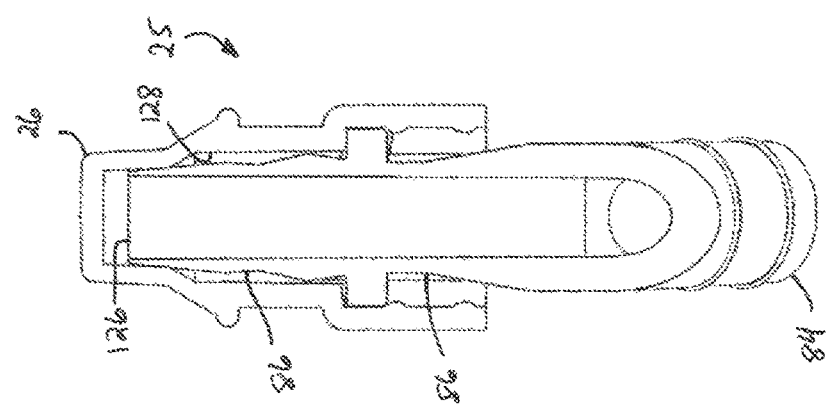
FIG. 40 is a first sequential depiction of a patient port assembly shown in latitudinal or coronal cross-section with the patient port cap element being shown in a first (rotative) position relative to the patient port elbow element for preventing air passage through the end orifice of the patient port assembly.

Referencing FIGS. 37 and 40 the reader will there note that the outer surfacing 86 of the elbow element 84 contact the internal surfacing 128 of the cap element 26 in the first rotative position for closing the patient port assembly 25. FIGS. 38 and 41 together depict the pressure equalization second or intermediate cap position whereby minimized airflow as at small arrow 129 is enabled for equalizing the pressure between the inner liner assembly 12 and the outer hard shell canister 117. Lastly, FIGS. 39 and 42 depict a third rotative cap position whereby maximized airflow as at large arrow 130 is enabled for unobstructed free flow of air via the patient port assembly 25. Airflow 129 is enabled in the second rotative position via the air intake aperture 131 formed in the patient port cap element 26. As earlier indicated, the patient port 33 is further preferably outfitted with a one-way flapper type valve as at 31, which flapper valve 31 is retained at the patient port site by way of a valve retainer structure 32.

Referring now to the transfer port 34 and the transfer port assembly 23 connected thereto, the transfer port assembly preferably comprises a 90-degree elbow element 91 preferably outfitted with a Luer lock assembly having a base element 18 and a cap element 17. Extending laterally from the upright portion 132 is a universal port 88 having a universal connection point for accepting either a female coupling as at 89 or a male coupling as at 90. Comparatively referencing FIGS. 44 through 48, the reader will there consider the 90-degree elbow element 91 with upright portion 132 and laterally extending novel universal port 88. The novel universal port 88 represents an improvement over state of the art ports of this type that are typically reservoir or line specific. The novelty or unique design features enables the transfer port assembly 23 to cooperate with differently sized and shaped connectors or transfer sets. To achieve this primary object, the universal port 88 preferably comprises a stepped (as at steps 135) and tapered outer port surface 133 and a smooth tapered inner port surface as at 134.

The stepped and tapered outer port surface 133 comprises an outer tapered slope as generally depicted and referenced at 136 and the smooth tapered inner port surface preferably comprises an inner tapered slope as generally depicted and referenced at 137. The outer and inner tapered slopes 136 and 137 are (uniformly and oppositely) angled relative to a central port axis 138 of the universal port 88, which central port axis is preferably orthogonal to the upright axis 139.

Figure 47:
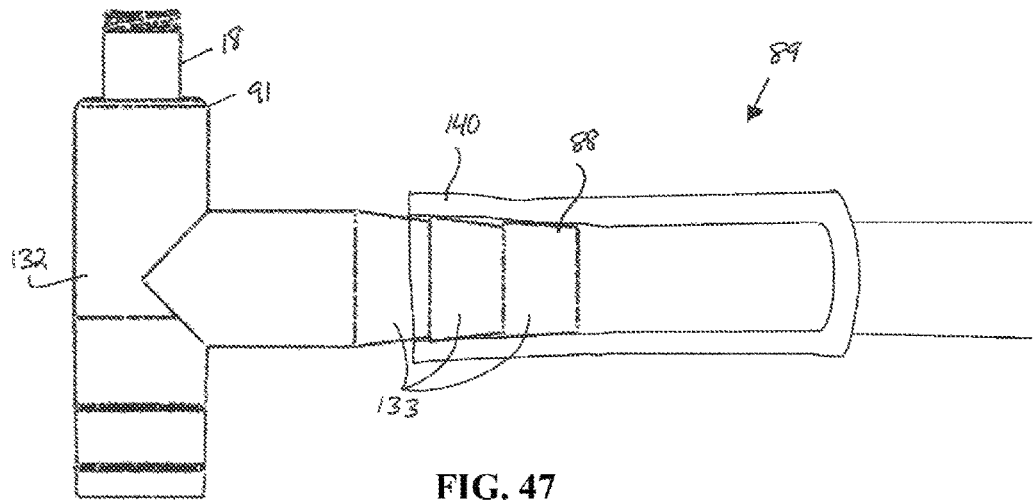
FIG. 47 is a lateral elevational view of the transfer port elbow element with universal coupling according to the present invention outfitted with a Luer lock base and a female line attachment attached to the universal coupling.
Figure 48:
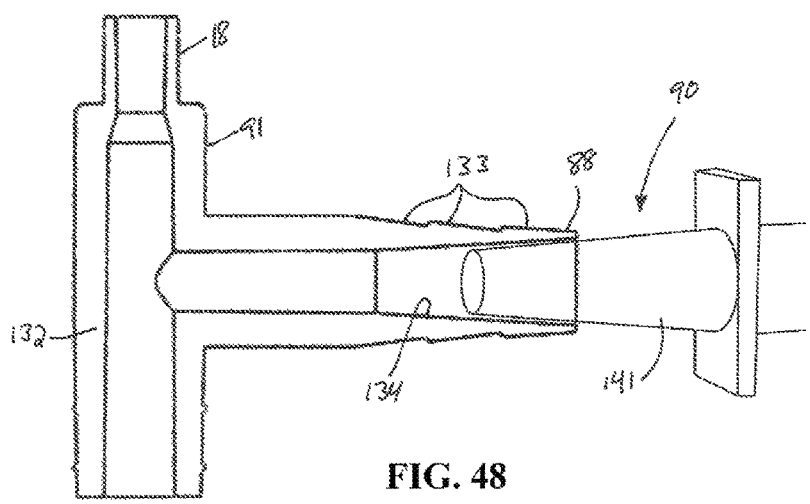
FIG. 48 is a medial cross-sectional view of the transfer port elbow element according to the present invention outfitted with a Luer lock base and a male line attachment attached to the universal coupling.
Figure 50:
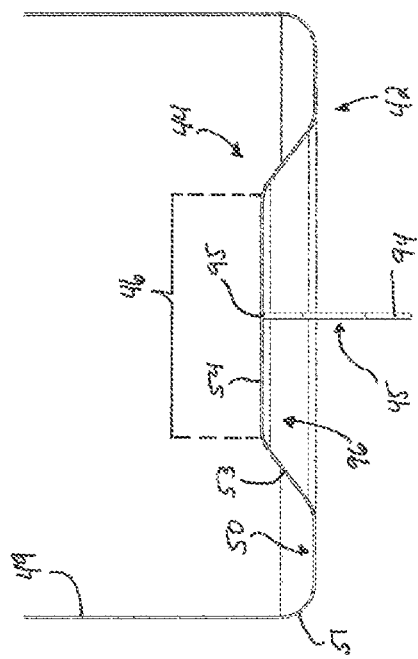
FIG. 50 is a longitudinal cross-sectional view of the lower liner bottom transversely through the hanger element in the extended position.
Figure 49:
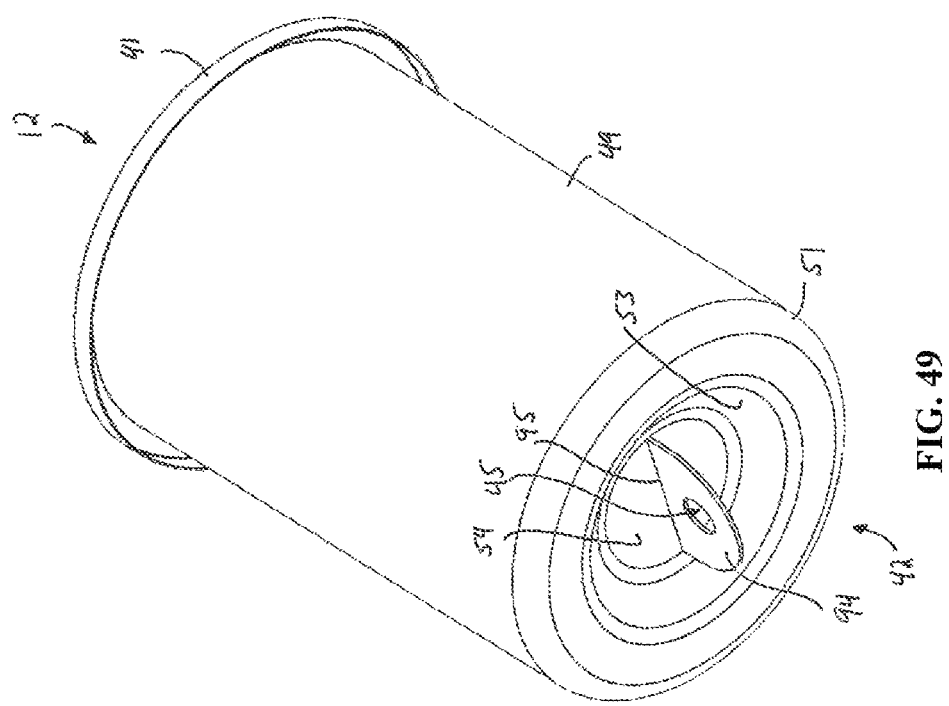
FIG. 49 is a bottom external perspective view of the liner assembly showing a hanger element in an extended position from an external hollow formation at the lower liner bottom.

Female connectors as generically depicted at 89 in FIG. 47 may thus resiliently engage the stepped and tapered outer port surface 133 such that the steps 135 and external diameters thereof cooperatively retain the resilient female ends 140 of the female connectors 89 in retained position upon the universal port 88. Male connectors as generically depicted at 90 typically comprise a sloped outer connector surface as at 141, which sloped outer connector surface comprises a tapered slope cooperable with the inner tapered slope 137 for mating the male connector(s) 90 with the universal port 88.

The internal port section 75 of transfer port 34 may be operably connected to either dip tube transfer assembly 27 in the case of the dip tube configuration or may be operably connected to a top drain filter assembly 87 in the case of a top drain configuration. When in the dip tube configuration, a Luer sample port (as at cap-base 17-18) may be preferably integrated with the 90-degree elbow structure 91 color coded blue. The Luer sample port enables (a) easy sterile sample access for canister contents 120 and (b) obstruction clearance by entraining air (under vacuum in normal use) to remove obstruction in novel way as no state of the art auto-transfusion reservoirs are capable of this function.

The transfer assembly 23 is preferably outfitted with a color-coded red twist transfer cap 24 threadably and solvent-attached (permanently) bonded to the transfer port 34. The transfer assembly 23 may be further outfitted with a Luer lock (cap-base) assembly as at 17-18 for blood sampling, clot dissipation and enabling further additive inputs. The additive port 35 may also be preferably outfitted with a 0.25 inch (28 thread) Luer lock (cap-base) assembly 17-18 as previously specified.

Figure 10:
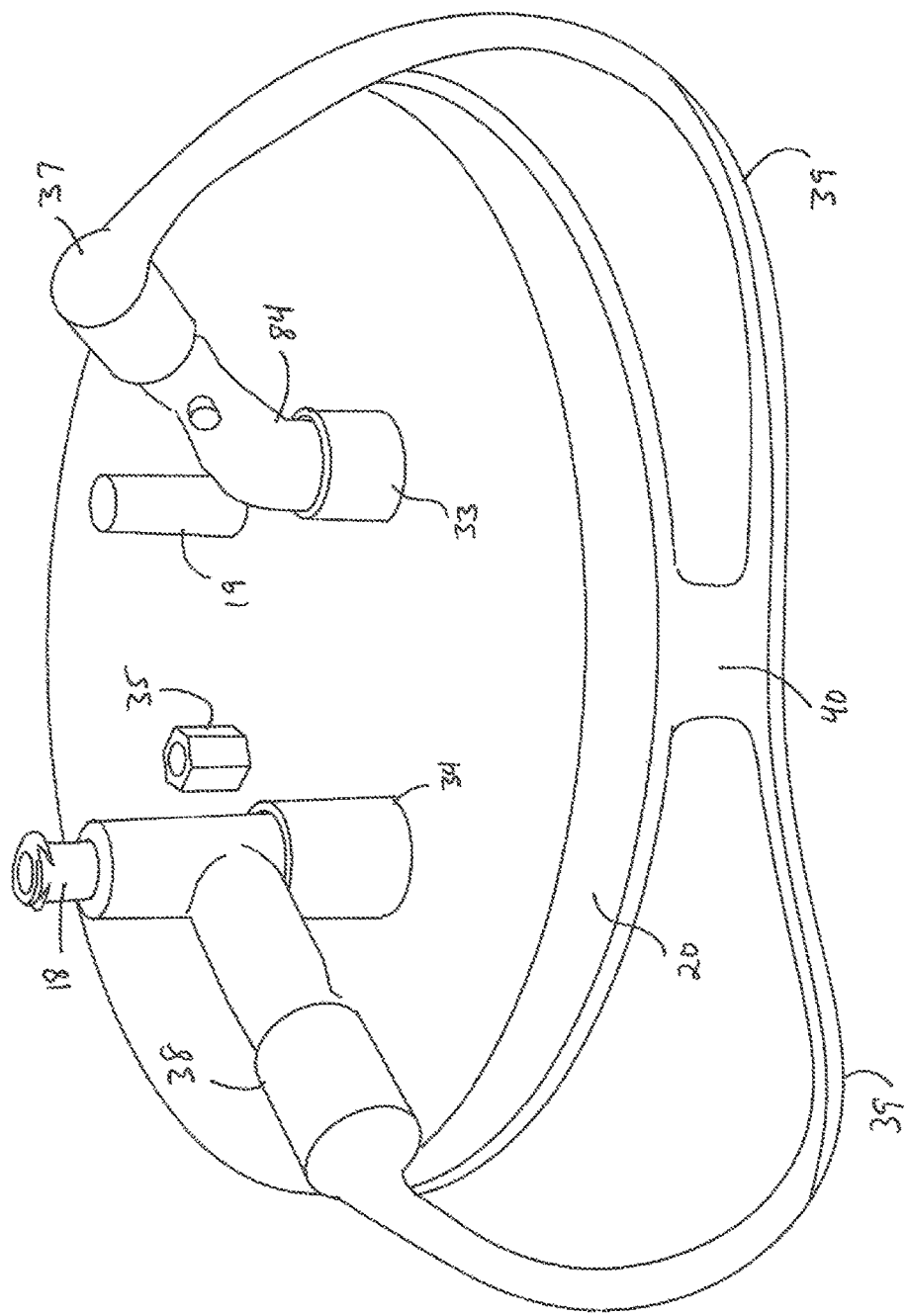
FIG. 10 is a top perspective view of a generic lid assembly according to the present invention showing tethered cap elements covering or capping the patient and transfer port orifices.
Figure 11:
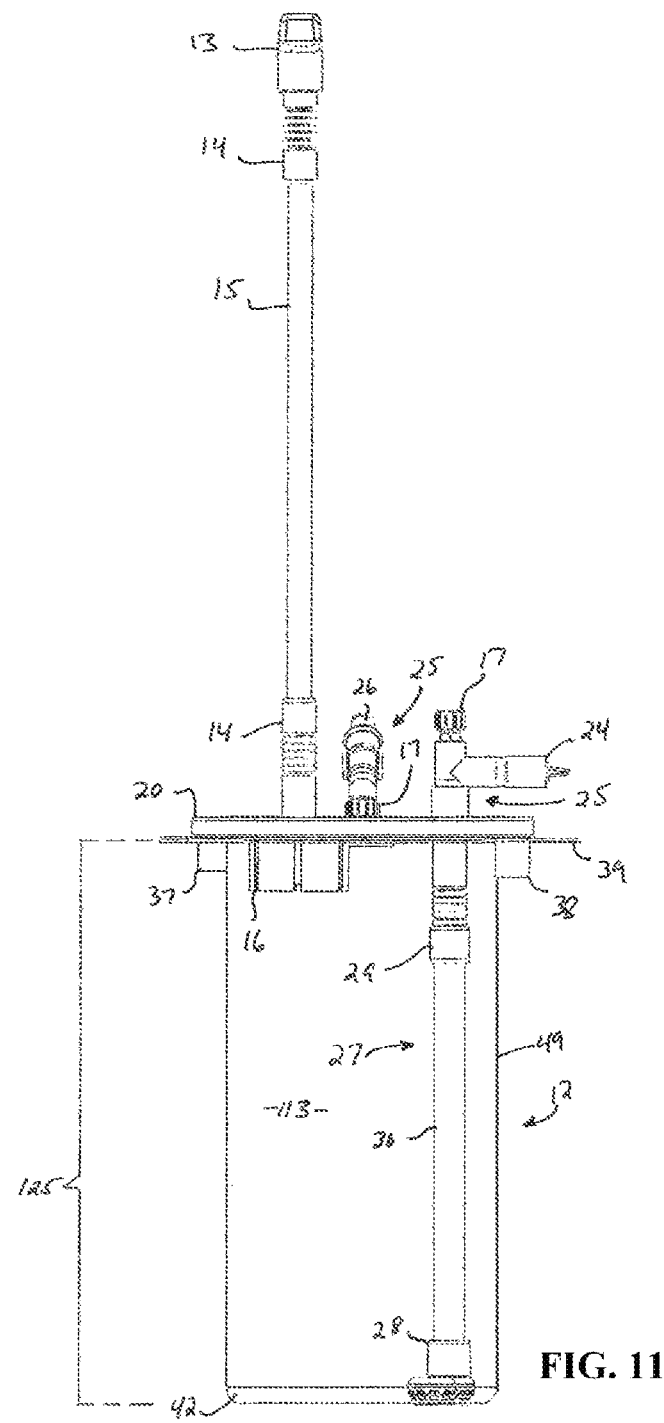
FIG. 11 is an assembled additive port side elevational view of the first alternative blood collection canister assembly according to the present invention showing a vacuum tube assembly, a dip tube assembly, and a liner assembly assembled with the primary lid portion.
Figure 12:
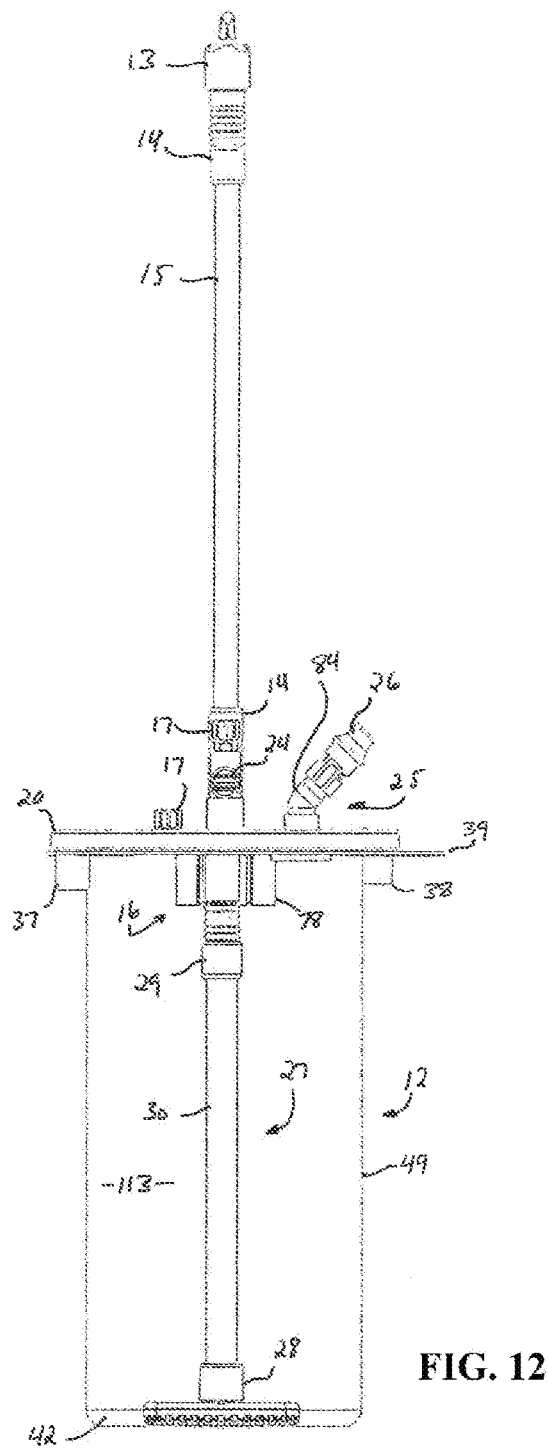
FIG. 12 is an assembled transfer port side elevational view of the first alternative blood collection canister assembly according to the present invention showing a vacuum tube assembly, a dip tube assembly, and a liner assembly assembled with the primary lid portion.

The primary lid portion 20 may be further preferably outfitted with an integrated IV hanging loop as at 36 and port line caps as at patient port cap 37 and transfer port cap 38 attached to the lid element 20 via integrated flexible tethers as at 39. FIG. 10 generally depicts the port line caps as at patient port cap 37 and transfer port cap 38 attached to the primary lid portion 20 via integrated flexible tethers 39 capping the orifices at the patient and transfer ports 33 and 34 for disposal purposes. The flexible tethers 39 are attached to the primary lid portion 20 via an anchor attachment formation as at 40.

Referencing FIGS. 11-22, the reader is there directed to various figures depicting the dip tube assembly 27 according to the present invention. The dip tube assembly 27 according to the present invention, as prefaced above, preferably comprises or includes a lower dip tube transfer filter element 28, an upper dip tube flex connector 29, and a dip tube conduit element 30 permanently bonded to the filter element 28. The dip tube conduit element 30 is preferably of a substantially rigid material construction having a 0.35 inch diameter. The upper dip tube flex connector 29 is attached to the dip tube conduit element 30 for enabling the dip tube conduit element 30 to bend out of axial alignment with the transfer port 34 for collapsing the flexible wall, fluid collection canister assembly 10 as further generally and particularly depicted in FIG. 23.

The dip tube assembly 27 cooperates with the liner assembly 12 for achieving maximum drainage of liner-collected materials or fluids (e.g. shed blood). Assembly 10 thereby provides for the simultaneous collection and transfer of blood without interruption of the surgical field. In this regard, the reader will further note that the liner assembly 12 preferably comprises an upper liner mouth 41, a lower liner bottom 42, a liner wall 49, and a generally cylindrical overall geometry for collecting or defining a maximum inner liner space 113 (e.g. 1300 mL or 1800 mL). The upper liner mouth 41 is received and preferably permanently attached (bonded) to a radially inner, mouth-receiving groove 43 of the primary lid portion 20 for attaching the liner assembly 12 to the lid assembly 11.

The lower liner bottom 42 may preferably comprise or include a central punt, kick-up or dimple feature as at 44. The dimple feature 44 comprises an upper radially inner dimple diameter as at 46 and a lower radially outer dimple diameter as at 47. The liner wall 49 preferably comprises or includes a substantially uniform liner wall diameter as at 48 when in a fully cylindrical form. Extending intermediate the dimple feature 44 and the liner wall 49 is a filter-receiving annular depression 50, which annular depression 50 basically comprises an outer diameter equal to the liner wall diameter 48 and an inner diameter equal to the outer diameter 47.

A liner bottom radius of curvature 51 may preferably connect or slope from the liner wall 49 to the annular depression 50 and a dimple slope 53 may extend from a central, planar, upper dimple portion 54 to a lower dimple portion 55. Shed blood 52 may thus flow into the annular depression 50 down the dimple slope 53 as generally depicted in FIGS. 16 and 17. Notably, the lower dip tube transfer filter element 28 comprises a filter footprint, which footprint is generally depicted and referenced in FIGS. 13 and 18 at 56 and which footprint 56 generally follows, cooperates with, or is received in an arc length segment (i.e. that arc length segment between broken lines 57) of the annular depression 50.

In this last regard, the lower dip tube transfer filter element 28 preferably comprises or includes a filter arc length form as at 59, a filter bottom portion as at 60, and a filter upper portion as at 61. The filter upper portion 61 comprises a tube connection portion 62 and an aperture opposing portion 63. The filter bottom portion 60 preferable comprises or includes a planar bottom as at 64 and a rounded wall 65 extending upwardly from the planar bottom 64. Both the planar bottom 64 and the rounded wall 65 preferably comprise (blood) intake apertures as at 66 and 67. The reader will note that the aperture opposing portion 63 of the filter upper portion 61 is solid and comprises no intake apertures.

The blood intake apertures 66 formed in the planar bottom portion 64 may preferably define a first aperture shape (e.g. square or rectangular) and the blood intake apertures 67 formed in the rounded wall 65 may preferably define a second aperture shape (e.g. a radius end as at 68 opposite a square or rectangular end as at 69). The apertures 67 may preferably be curved in vertical transverse cross-section to follow the cross-section of the rounded wall 65 such that radius ends 68 are oriented toward the planar bottom 64.

The filter element 28 is preferably toleranced to or spaced from the liner bottom 42 for removing a maximum amount of canister contents 120 and the aperture dimensions, on the order of 0.125 inches, are sufficiently sized to remove particulate matter of the canister contents larger than this and thus easily enable the transfer or particles on the order of 6-8 microns, the average diameter of a typical Red Blood Cell or RBC. The transfer filter 28 is thus seatable in the annular depression 50 for filtering blood collected in the annular depression 50 and transferable via the dip tube assembly 27.

Referencing FIGS. 26 and 28-30, the reader will there consider various aspects of a second alternative embodiment of the flexible wall, fluid collection canister assembly according to the present invention as generally depicted and referenced at 110. The flexible wall, fluid collection canister assembly 110 according to the present invention provides the so-called top drain configuration whereby shed blood is typically collected for evaluation purposes or for processing with an auto-transfusion device.

The top drain filter assembly 87 comprises an integrally formed filter-cap element whereby the filter portion 92 may function to prevent particles greater than 6-8 microns from passing therethrough so as to prevent obstructions in the transfer port 34, transfer tube or transfer line 93 (one end red and one end blue with an optional Roberts clamp 99) to the auto-transfusion device. Optional Roberts clamps 99 may thus be incorporated into the overall system and attached to and set to the off position for selectively preventing passage of blood therethrough when required.

The top drain configuration further contemplates the integration of a hanger and/or bracket element as at 94, which bracket element 94 preferably incorporates a living hinge as at 95 for enabling ease of storage as the hanger element is sized and shaped to nest in the external hollow 96 formed by dimple feature 44. Compared to the dip tube configuration, the top drain configuration enables relatively greater folding potential to allow relatively more compact shipping, storage, and disposal thereby resulting in increased economics due to fewer components and increased storage.

Figure 52:
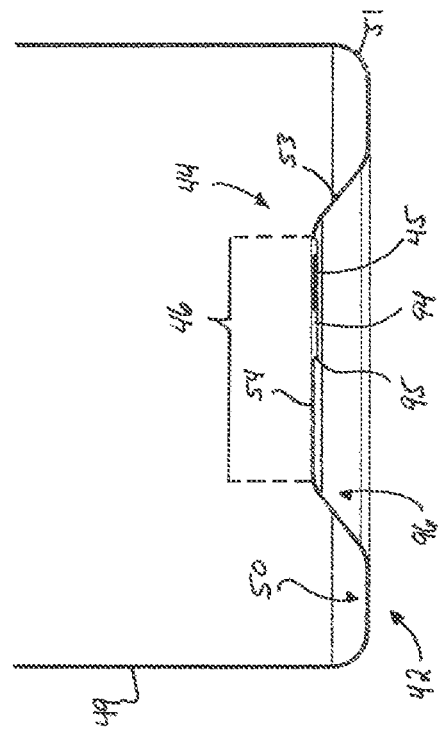
FIG. 52 is a longitudinal cross-sectional view of the lower liner bottom transversely through the hanger element in the stowed position.
Figure 51:
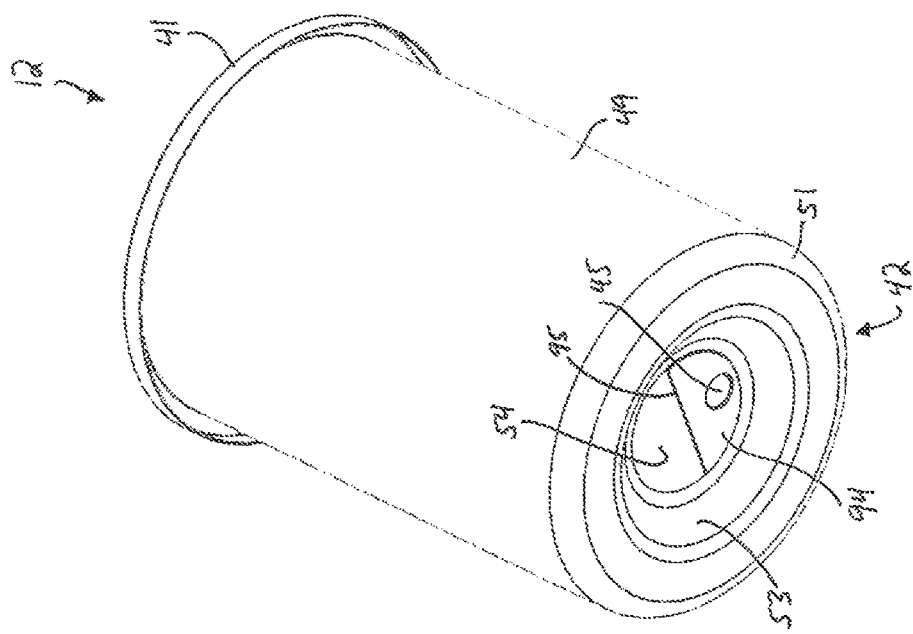
FIG. 51 is a bottom external perspective view of the liner assembly showing the hanger element in a stowed position within the external hollow formation of the lower liner bottom.

Referencing FIGS. 49-52, the reader will revisit the lower liner bottom 42 having a central punt, kick-up or dimple feature 44 forming an external hollow as at 96. Noting that the dimple feature 44 with external hollow 96 comprises an upper radially inner dimple diameter 46, the reader will further note that the hanger element 94 with support-receiving aperture 45 is attached to external surfacing of the central upper dimple portion 54 and comprises a semicircular shape having a diameter substantially equal to or less than the upper radially inner dimple diameter 46, which diameter corresponds with the living hinge 95 thereby attaching the hanger element 94 to the dimple feature 44. When not in hanging use, the hanger element 94 may thus be folded into a hanger element stowed position as generally depicted in FIGS. 51 and 52 for allowing or enabling relatively more compact shipping, storage, and disposal.

It will be further recalled that the primary lid portion 20 preferably comprises a radially inner, mouth-receiving groove 43 for attaching the liner assembly 12 to the lid assembly. The primary lid portion 20 further preferably comprises a radially outer, mouth-receiving groove as at 119 for receiving the upper hard shell canister mouth 118 of a hard shell canister 117. The radially outer mouth-receiving groove 119 is preferably outfitted with periodically spaced tab elements as at 121, which tab elements 121 resiliently engage an outer peripheral flange 122 formed on the mouth 118. The flexible wall, fluid collection canister assemblies according to the present invention are thus usable in combination with a hard shell canister 117 made possible via the connectivity of the primary lid portion 20 to the mouth 118, preferably of a snap fit type construction.

Figure 31C:
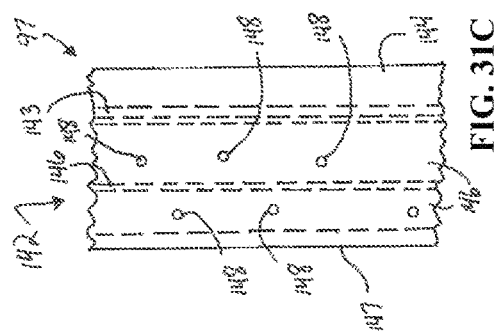
FIG. 31C is an enlarged diagrammatic detailed view of the multi-layered bio-coating as enlarged from FIG. 31B to show in diagrammatic detail the various functional layers of the bio-coating for preventing thrombosis formations within the Aspiration and Anticoagulation (AA) line.
Figure 31:
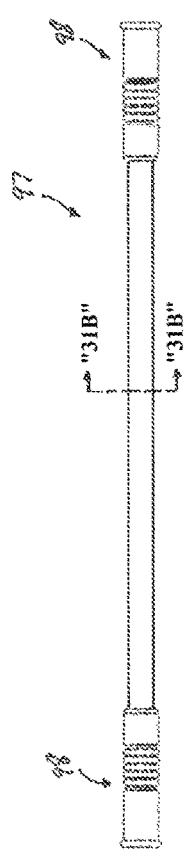
FIG. 31 is a side view of a bio-coated single lumen Aspiration and Anticoagulation (AA) line according to the present invention.
Figure 31B:
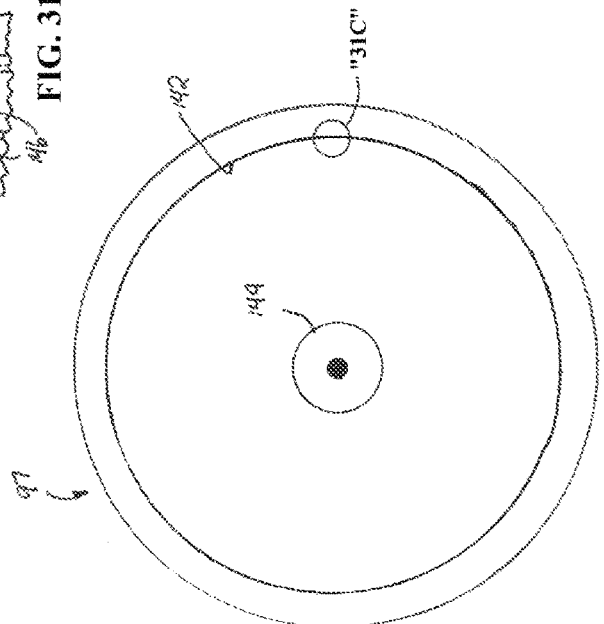
FIG. 31B is an enlarged transverse cross-section of the Aspiration and Anticoagulation (AA) line as sectioned from FIG. 31 depicting the blood transfer line with a bio-coating and an inner line surfacing without thrombosis formations thereby maintaining a maximum transfer force within the coated line.

An Aspiration and Anticoagulant Line (AA Line) 97 is further generally and simply depicted in FIG. 31. This AA Line 97 provides a bio-coated single lumen line to eliminate the use of dual lumen AA lines which are complex, expensive and not end-specific. The bio-coated single lumen line as at AA line 97 may preferably comprise color coded ends 98 to differentiate between viable blood and waste blood collection in contradistinction to state of the art line provisions. Either end 98 is compatible with sterile surgical field, canister or wound drainage.

The bio-coated AA Line 97 may preferably be outfitted with a bio-coating as exemplified by the ASTUTE® brand Advanced Heparin Coating sold via Biointeractions, Ltd. of Earley Gate, Whiteknights Road, University of Reading Science & Technology Center, Reading, Berkshire UNITED KINGDOM. The ASTUTE® brand Advanced Heparin Coating generally and directly negates the adverse biological responses that are initiated when blood makes contact with a foreign surface, such as platelet/protein adhesion, platelet activation and blood clot or thrombosis formation.

In this last regard, it is contemplated that the AA line 97 may also be preferably utilized as a suction or blood transfer line (e.g. as at tubing 85). It is noted that state of the art suction lines without a bio-coating often clot or become easily obstructed thereby impeding the suction force for driving material there through. In a surgical field, this is highly problematic and poses a significant threat to patients if bleeding occurs and irrigation cannot be properly applied to the wound site due to impeded suction lines.

Referencing FIGS. 31-31C the reader will consider the AA line or suction line 97 preferably outfitted with a bio-coating as at 142 for preventing clot or thrombosis formation within the line 97. The bio-coating may be preferably exemplified by a priming layer or layers 143 as attached to an outer substrate 144 or material construction of the conduit or line. A sulfate or sulfonate layer 145 appears as in inner adjacency to the priming layer 143 from which layer 145 hydrated polyethylene glycol chains extend as at layer 146. A cross-linking layer 147 is interwoven in the layer 146 with covalent bond sites as at 148 and an inner function layer of heparin molecules as at layer 147.

Figure 31A:
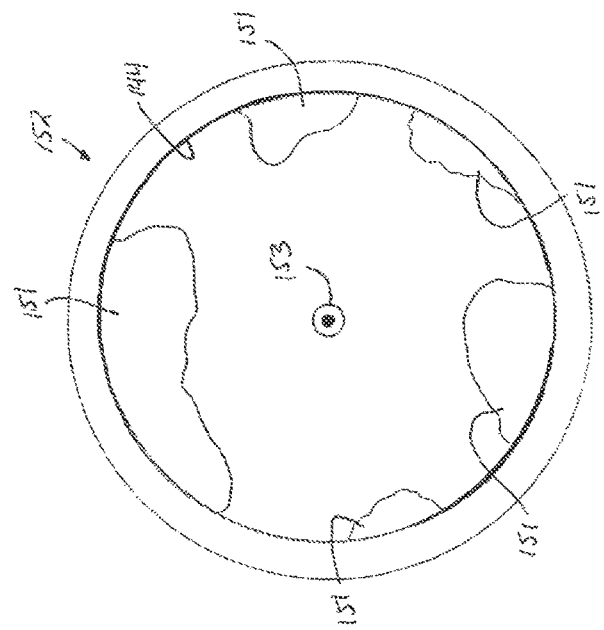
FIG. 31A is an enlarged transverse cross-section depiction of a blood transfer line without a bio-coating and depicting thrombosis formations within the line thereby reducing the net transfer force within the uncoated line.
Figure 33:
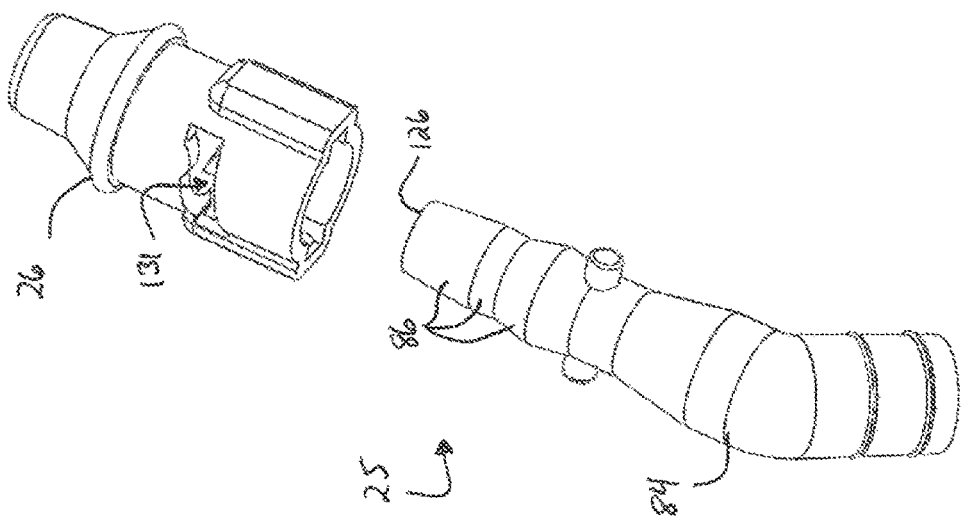
FIG. 33 is an exploded top perspective view of the patient port assembly according to the present invention showing the patient port cap exploded from the patient port elbow element.
Figure 32:
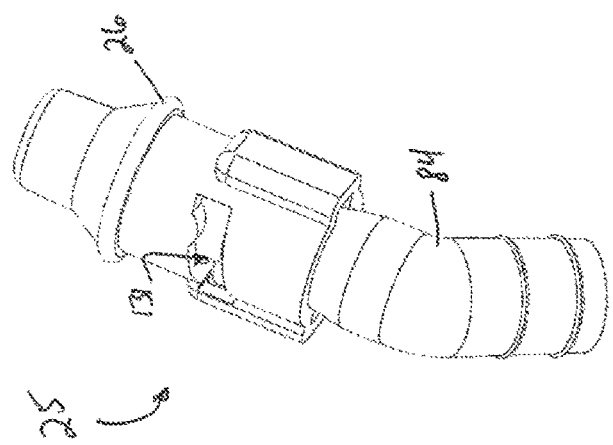
FIG. 32 is a top perspective view of a patient port assembly according to the present invention showing a patient port cap in assembled relation with a patient port elbow element.
Figure 36:
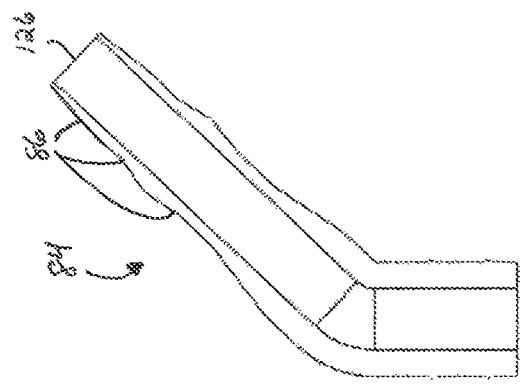
FIG. 36 is a medial cross-sectional view of a patient port elbow element according to the present invention.
Figure 35:
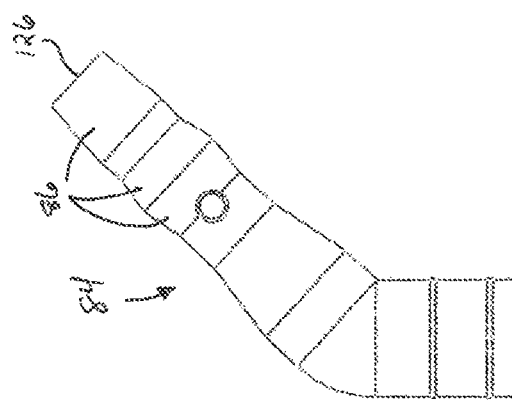
FIG. 35 is a lateral elevational view of a patient port elbow element according to the present invention.
Figure 34:
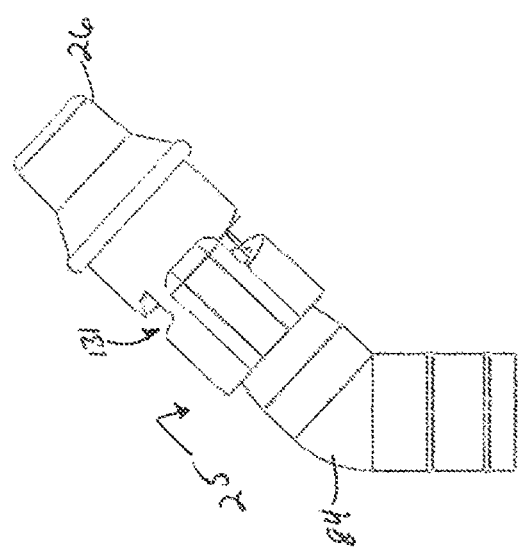
FIG. 34 is a lateral elevational view of a patient port assembly according to the present invention showing a patient port cap in assembled relation with a patient port elbow element.

When the outer substrate layer 144 is outfitted with the bio-coating as exemplified by the foregoing, thrombosis formation is hampered if not prevented as generally depicted in FIG. 32B depicting a relatively large diameter force vector heading out of the page as at 149. The inner bio-coated wall as at 142 is free from blood clots as otherwise shown in FIG. 31A, which figure depicts a suction line without a bio-coated simple substrate layer as at 144. Blood clot 151 formation is thus evident within the line 152 and a relatively small diameter force vector heading is indicated at 153.

If an attending surgeon is unable to visualize a wound site because s/he is unable to irrigate the site due to clogged or ineffective suction lines as at line(s) 152 the patient is placed at greater risk. To clear obstructions from a suction line such as blood clots or massive thrombosis sites as at 151, saline must typically be flushed through the line 152 to clear the clots 151, or in some cases, a new suction line must be deployed to replace the clogged line 151 if the obstruction(s) cannot be cleared. The AA line 97 or suction line 97 according to the present invention is thus beneficial at least insofar as its ability to decrease or slow the activation of blood within a suction line for non-sterile collection of blood via a maximized irrigating force 149.

Both the dip tube configuration or embodiment (i.e. flexible wall, fluid collection canister assembly 10) and the top drain configuration or embodiment (i.e. flexible wall, fluid collection canister assembly 110) preferably comprise seated sterile caps to provide completely sealed canister ports for sterile storage of canister contents 120 for transfer to a blood bank for processing (or non-point of care processing) or direct reinfusion. Color coding is included for simple intuitive use on all ports and connections.

It will be noted that the color green is further and particularly contemplated for indicating recyclable potential and is believed novel at least insofar as blood collection has been traditionally associated with red and blue coloration schemes in the industry to demote arterial and venous blood sources. The green color coding boldly differentiates the intended use as not to be confused with waste collection. State of the art auto-transfusion systems do not currently incorporate such color coding schemes.

It will thus be understood that the present invention is primarily designed to provide a novel flexible fluid collection canister optionally usable in combination with a hard shell canister or housing and single lumen bio-coated AA line. The flexible canister assembly according to the present invention centers on or basically provides a lid assembly attached to a flexible liner assembly as at 12. The lid assembly is provided in two basic forms, the first as a so-called dip tube configuration or embodiment as part of canister assembly 10 as at lid assembly 11; and the second as a so-called top drain configuration or embodiment as part of canister assembly 110 as at lid assembly 111.

Both lid assemblies provide a one way inlet fluid port (i.e. patient port 33); a Luer port for administration of drugs/anticoagulant (i.e. additive port 35); a hook loop as at 36 for hanging/storage; connected/non-connected sterile dead end caps as at 37 and 38 for fluid containment; a vacuum port as at 19 that is filtered and hydrophobic to maintain sterility; and a universal male/female transfer port as at 34 with Luer port (cap-base assembly 17-18) for sampling and clot removal.

The transfer port 34 may be connected to a filtered dip tube 30 that is toleranced or cooperably associated with liner bottom 42 to remove maximum amount of fluid under vacuum. The filter portion 28 of the dip tube assembly 27 obstructs particles from obstructing the dip tube 30 and transfer port 34. The filter pore size may be anything larger than 6 micron (RBC size) to diameter of dip tube 30 itself. The dip tube 30 is connected specifically by a "flex" connector as at 29 to the primary lid portion 20. This flex connector 29 allows for the folding of the flexible liner wall 49 to enable compact storage for shipping and space requirements. This is novel in the fact that hard shell reservoirs require "empty space" utilization with both increased logistic expenses along with using valuable real estate in an operating room.

In one embodiment or deployment, the flexible liner assembly 12 is placed inside a hard shell holder or canister 117 and connected to vacuum. Vacuum is established and the patient port cap 26 is designed to cam twist 45 degrees to release the vacuum port 19 to open air to equalize pressure between the flexible liner assembly 12 and the hard shell canister 117 while maintaining sterility. The patient blood port cap 26 can then rotate to close to allow liner element 12 to "seat" in hard shell canister 117 until connected to the AA line 97. The AA line 97 is handed up sterile to operative field and either end may be passed off of operative field to be connected to patient port 33.

Measured anticoagulant may then either be placed in the canister assembly 10 through "additive" Luer type port 35 or mixed titrated at entry point to canister assembly 10 and AA line 97. The operative end of the AA line 97 may be connected to desired suction wand apparatus. Shed blood/fluid enters the AA line 97 and bio-coating protects the shed blood from short term activation until blood is mixed via canister reservoir or titrated at entry of patient fluid port 33. The blood/fluid is collected until determination is made to start processing with an auto-transfusion device (e.g. Cell Saver) or for storage or disposal. Also in this embodiment, the AA line 97 may be connected to a wound drain for closed drainage vs. wand.

In a processing embodiment or deployment, the auto-transfusion device is connected to the blood recovery device transfer port 34 that is universal in design (Male and Female port types as at point 88) to accommodate various/multiple manufacturer auto-transfusion device designs as at 89 and 90. Once sterile connection is made, the auto-transfusion device may pull the collected blood/fluid unto itself for centrifugation of shed blood/fluid and washing of red blood cell mass for return to the patient 150.

In a storage embodiment or deployment, the blood recovery device or canister assembly according to the present invention may be capped with sterile connected provided caps as at 37 and 38 to maintain a fluid sterile barrier and may be placed on flat surface or hung from an IV pole or the like by the integral hook loop 36 of the primary lid portion 20. The blood recovery device or canister assembly may be transported to other areas for later processing as point of care or by a blood bank, following all FDA requirements, or alternatively filtered/reinfused to the patient 150.

In a disposal embodiment or deployment, if shed blood becomes contaminated, or there is very little blood loss, or blood removed for processing, the blood recovery device or canister assembly according to the present invention may have the contents removed via transfer port 34 for waste disposal and/or capped for biohazard disposal. The economic advantages of the blood recovery device or canister assembly according to the present invention primarily stem from the light weight construction and decreased volume for biohazard waste cost constraints.

While the foregoing specifications set forth certain specificity, the same should not be construed as setting forth limits to the invention but rather as setting forth certain preferred embodiments and features. For example, as prefaced hereinabove, it is contemplated that the present invention essentially provides a blood collection canister assembly as at 10 or 110 for collecting and transferring blood. The blood collection canister assemblies according to the present invention preferably and essentially comprise or include a liner assembly as at 12 and a lid assembly as at 11 or 111.

Figure 13:
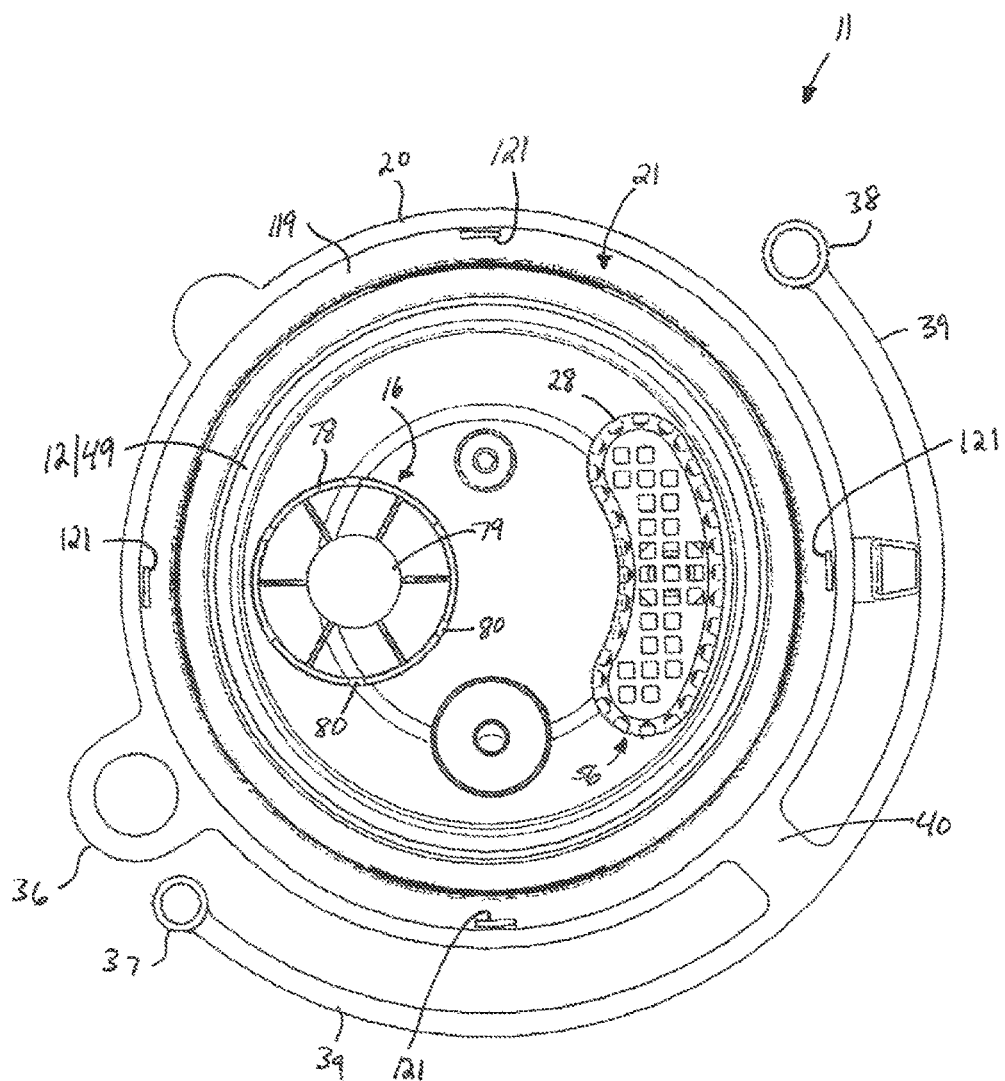
FIG. 13 is a bottom plan view of the first alternative blood collection canister assembly according to the present invention with parts of the lower liner bottom broken away to more clearly show lid assembly structures.
Figure 14:
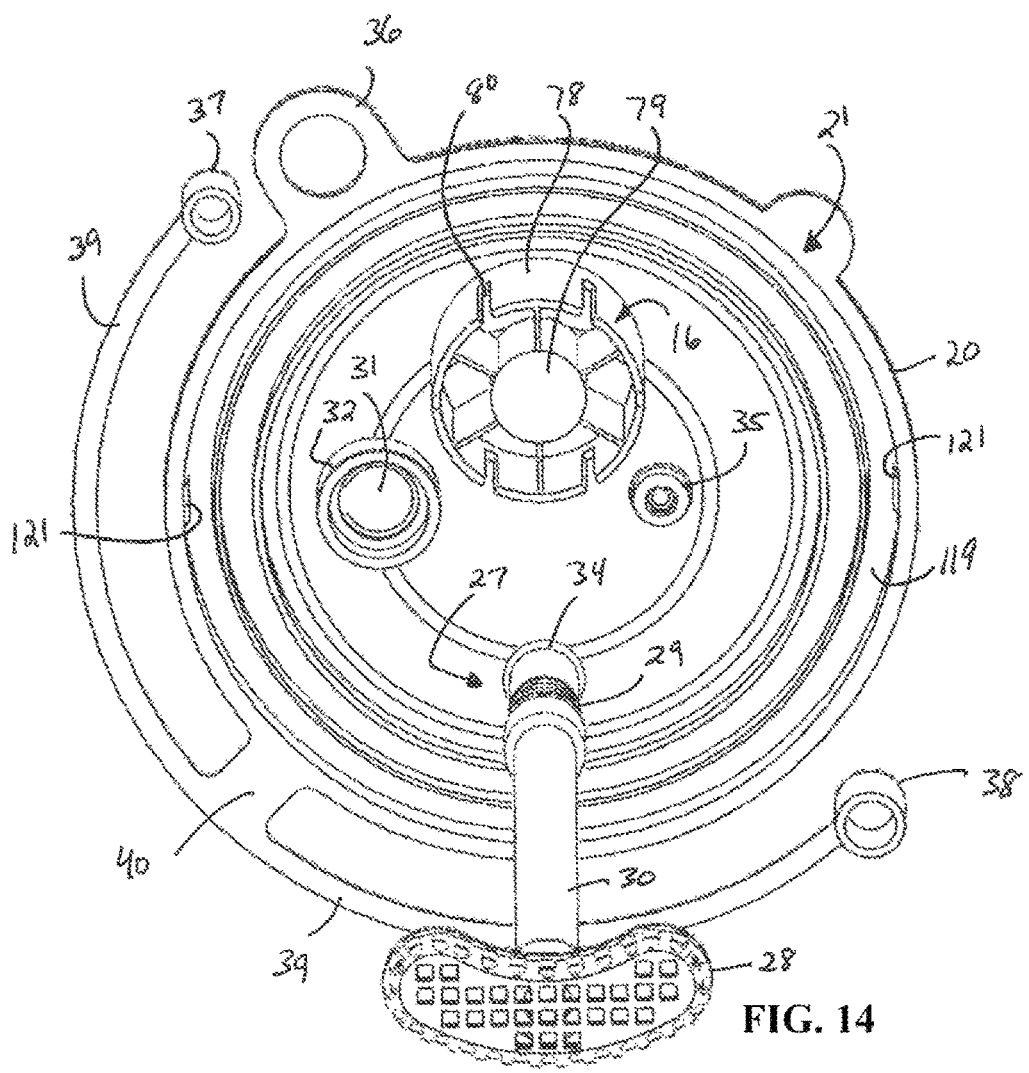
FIG. 14 is a bottom perspective view of the first alternative lid assembly according to the present invention.
Figure 15:
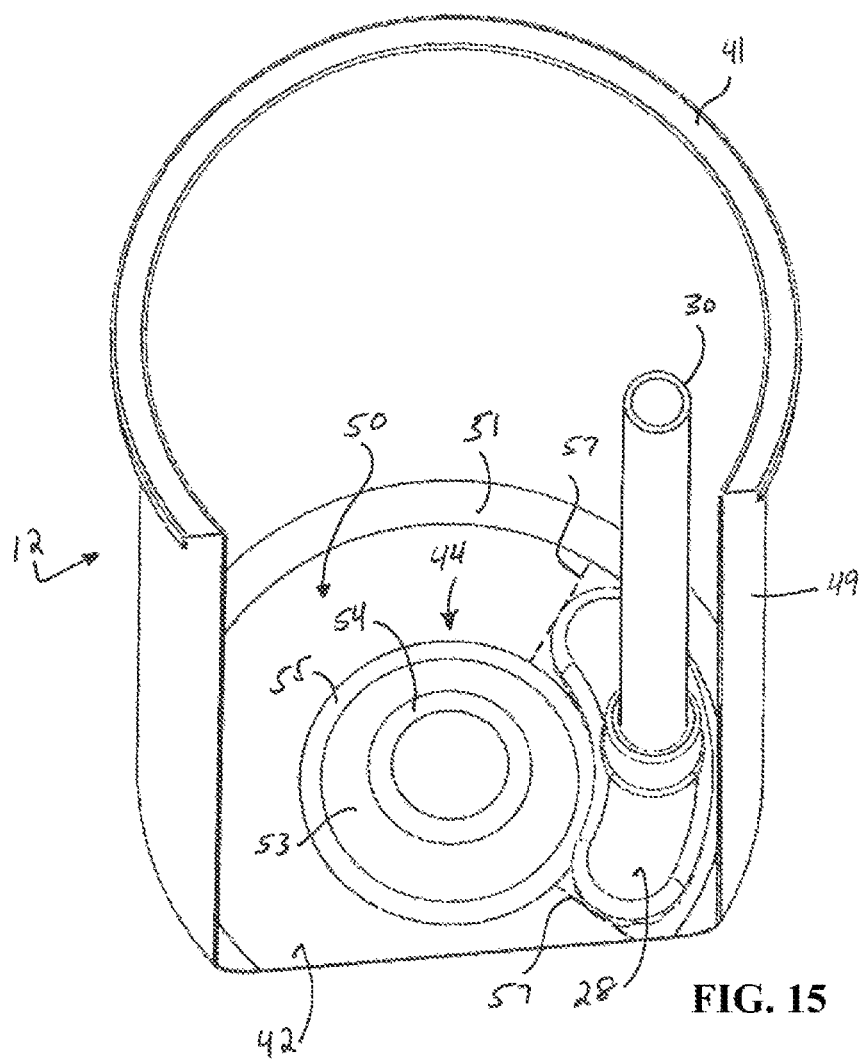
FIG. 15 is a fragmentary top perspective view of the liner assembly and dip tube assembly with parts broken away to more clearly show the structural relationship between bottom portions of the dip tube assembly and the liner assembly.

The liner assembly 12 preferably comprises a flexible liner material and a cylindrical liner form having a circular transverse liner cross-section as generally depicted in FIG. 13, a liner height 125 and an upper liner mouth as at 41. The cylindrical liner form defines an inner liner space as at 113. The lid assemblies each preferably and essentially comprise a primary lid portion as at 20, which primary lid portion 20 is attachable to the upper liner mouth 41 and comprises a series of ports including a vacuum port 19, a patient port 33, and a transfer port 34 and at least one additive port 35 for enabling the user to add material to the inner liner space 113.

Figure 4:
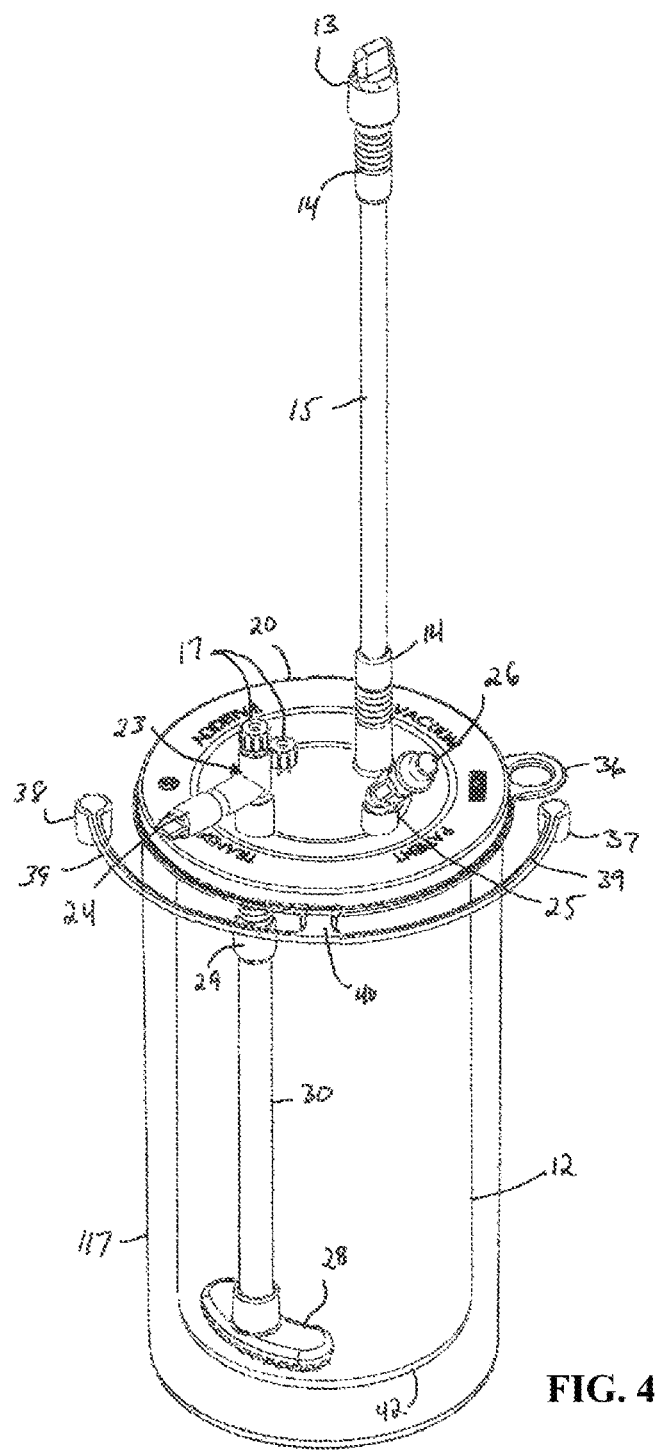
FIG. 4 is an assembled top perspective view of a first alternative blood collection canister assembly according to the present invention showing a vacuum tube assembly, a dip tube assembly, a liner assembly, and a hard shell canister assembled with the first alternative lid assembly.
Figure 4A:
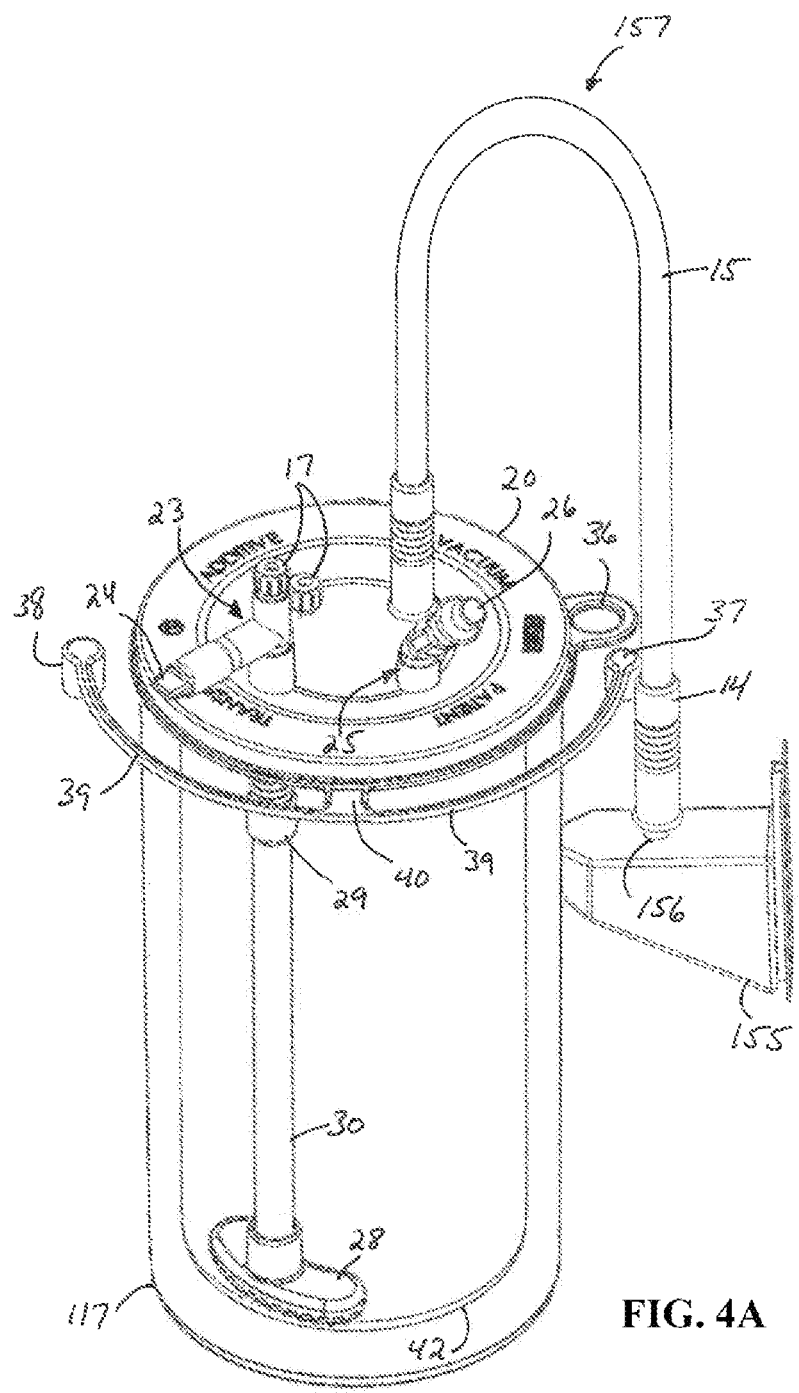
FIG. 4A is an assembled top perspective view of a first alternative blood collection canister assembly according to the present invention partially received in/exploded from an external hard shell canister assembly outfitted with a vacuum assembly.

The vacuum port 19 communicates with a vacuum line as at 15 and an external vacuum source for directing blood transfer from a patient 150 via the blood collection canister assembly. In this regard, the reader is directed to FIG. 4A, which figure depicts blood collection canister according to the present invention with primary lid portion 20 and liner assembly 12 partially receive in and/or exploded from a hard shell canister 117 in communication with a vacuum source 155. The vacuum source 155 comprises a vacuum port as at 156 coupled to the flex connector 14 opposite the flex connector 14 coupled to the vacuum port 19. The vacuum line 15 can be bent into an arch formation as at 157 leading downwardly to the vacuum port 156 and thus provides a gravity-based mechanical barrier for the prevention of contamination due to condensation, etc.

The patient port 33 receives directed blood transfer from the patient 150, and the transfer port 34 enables transfer of collected blood to a separate external reservoir or processing device or system for further processing. The blood collection canister assembly according to the present invention is usable in either an upright, first configuration as generally depicted in FIG. 1 or 27 for collecting blood and usable in an inverted, second configuration as generally depicted in FIG. 26 for transferring collected blood.

The vacuum port 19 is preferably outfitted with a hydrophobic barrier as at vacuum filter element 79 which element 79 absorbs blood if canister contents levels become too high within the inner space 113. The hydrophobic barrier thus functions to seal canister contents from the external vacuum source and prevent overfill of the liner assembly with canister contents. The vacuum port 19 may further be preferably outfitted with a shroud element as at 78 having blood-outletting slots 80. The blood-outletting slots 80 preferably comprise or include terminal slot extents as at 82 for permitting blood overspill into the inner liner space 113 when the blood collection canister assembly 110 is in the inverted, second configuration for transferring collected blood via the transfer port as outfitted with the top drain filter assembly 87.

Figure 19:
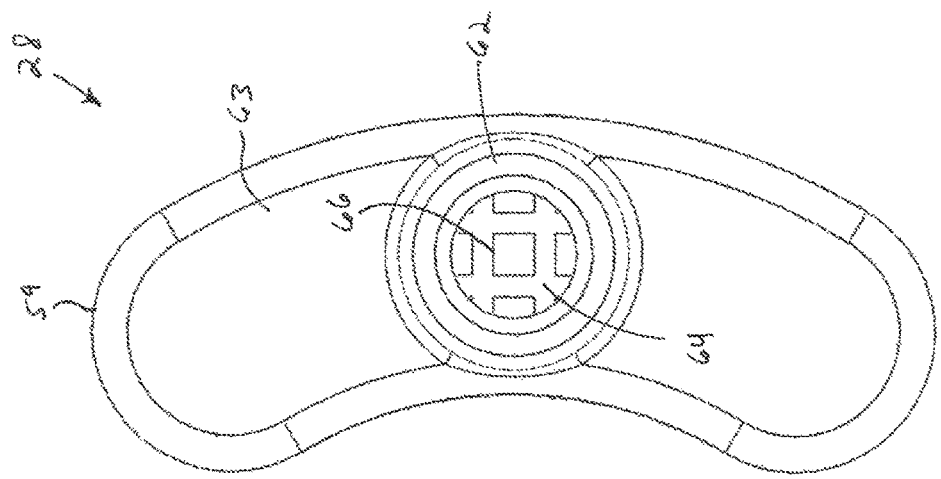
FIG. 19 is a top plan view of the dip tube transfer filter element according to the present invention.
Figure 18:
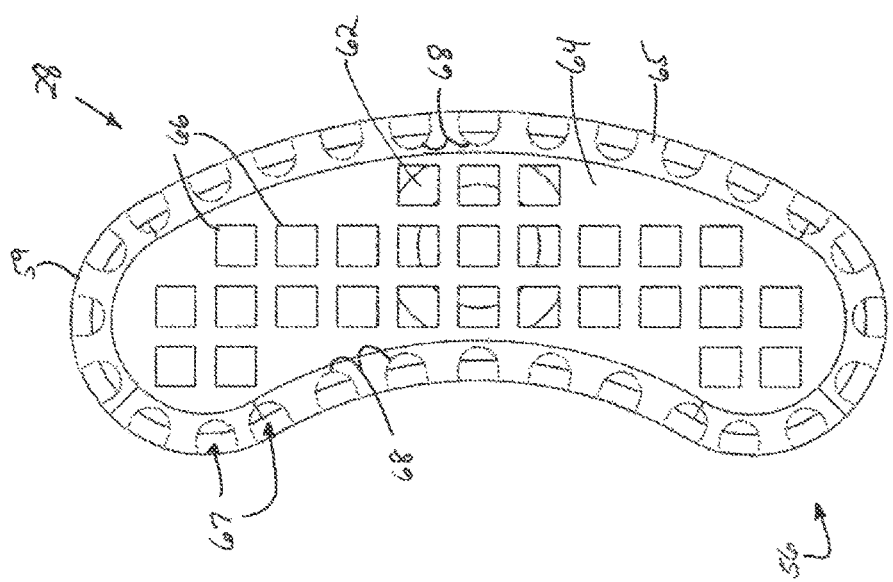
FIG. 18 is a bottom plan view of a dip tube transfer filter element according to the present invention.

The dip tube assembly 27 is connectable to the transfer port 34 and usable in the upright, first configuration in combination with the transfer port for transferring collected blood or container contents 120 to a separate reservoir such as a blood bag, a blood bank, auto-transfusion device or waste disposal unit for further processing. The liner assembly 12 may preferably comprise or include a liner bottom 42 having an annular depression as at 50. The dip tube assembly 27 preferably comprises or includes a transfer filter 28 having a filter arc length as generally depicted in FIGS. 18 and 19, and a filter bottom portion as at 60 seatable in the annular depression 50 for filtering blood collected in the annular depression 50 and transferable via the dip tube assembly 27.

The liner bottom comprises a dimple feature 44 such that the transfer filter 28 is seatable in the annular depression 50 in radial adjacency to the dimple feature 44. The dimple feature 44 may preferably provide an external hollow 96 and comprises an inner dimple diameter 46 at a planar upper dimple portion 54. A hanger element 94 may be preferably externally and hingedly attached to the dimple feature 44 within the external hollow 96 via a living hinge mechanism 95.

The hanger element 94 may be outfitted with an aperture 45 for enabling the user to hang the canister assembly 110 in the inverted, second configuration. The hanger element 94 may preferably comprise a hanger diameter at its semicircular portion that is cooperable with the inner dimple diameter 46 for enabling the hanger element 94 to fold into a stowed position within the external hollow 96 in adjacency to the planar upper dimple portion 54. The dimple feature 44 and hanger element 94 thus for enhance functional and stowage characteristics of the blood collection canister assembly 110.

The filter bottom portion 60 preferably comprises a planar bottom 64 and a rounded wall 65 extending upwardly from the planar bottom 64. The planar bottom 64 and the rounded wall 65 preferably comprise blood intake apertures as at 66 and 67 or a blood intake grating forming said apertures. The blood intake apertures 66 formed in the planar bottom 64 may preferably define a first aperture shape (e.g. square or rectangular) and the blood intake apertures 67 formed in the rounded wall 65 may preferably define a second aperture shape (radiused or rounded at a first end towards the planar bottom 64 and square or rectangular at a second end opposite the planar bottom 64).

Figure 23:
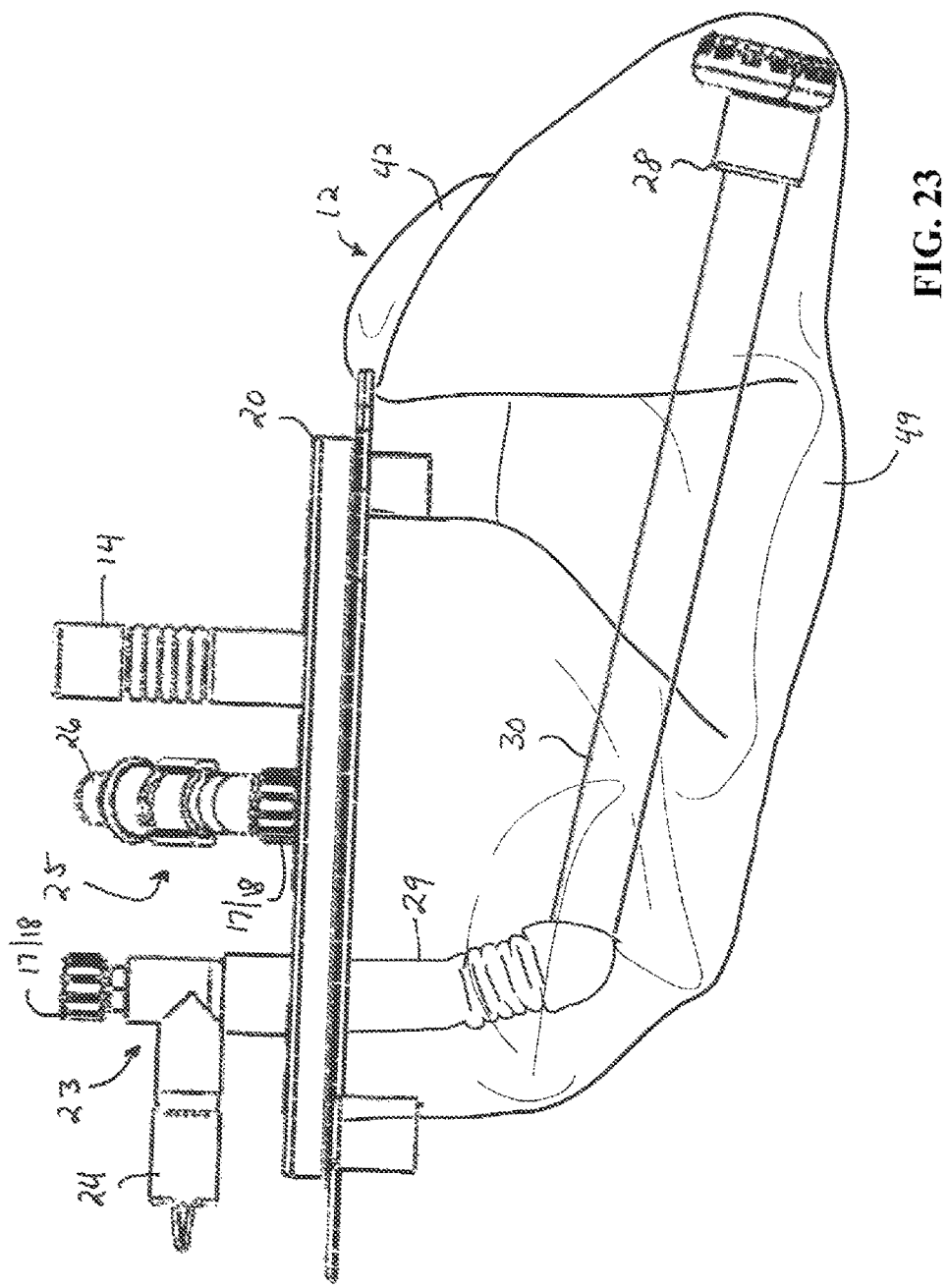
FIG. 23 is an additive port side schematic depiction of the first alternative blood collection canister assembly according to the present invention shown in a collapsed state with the dip tube transfer assembly shown bent out of axial alignment with the transfer port.
Figure 24:
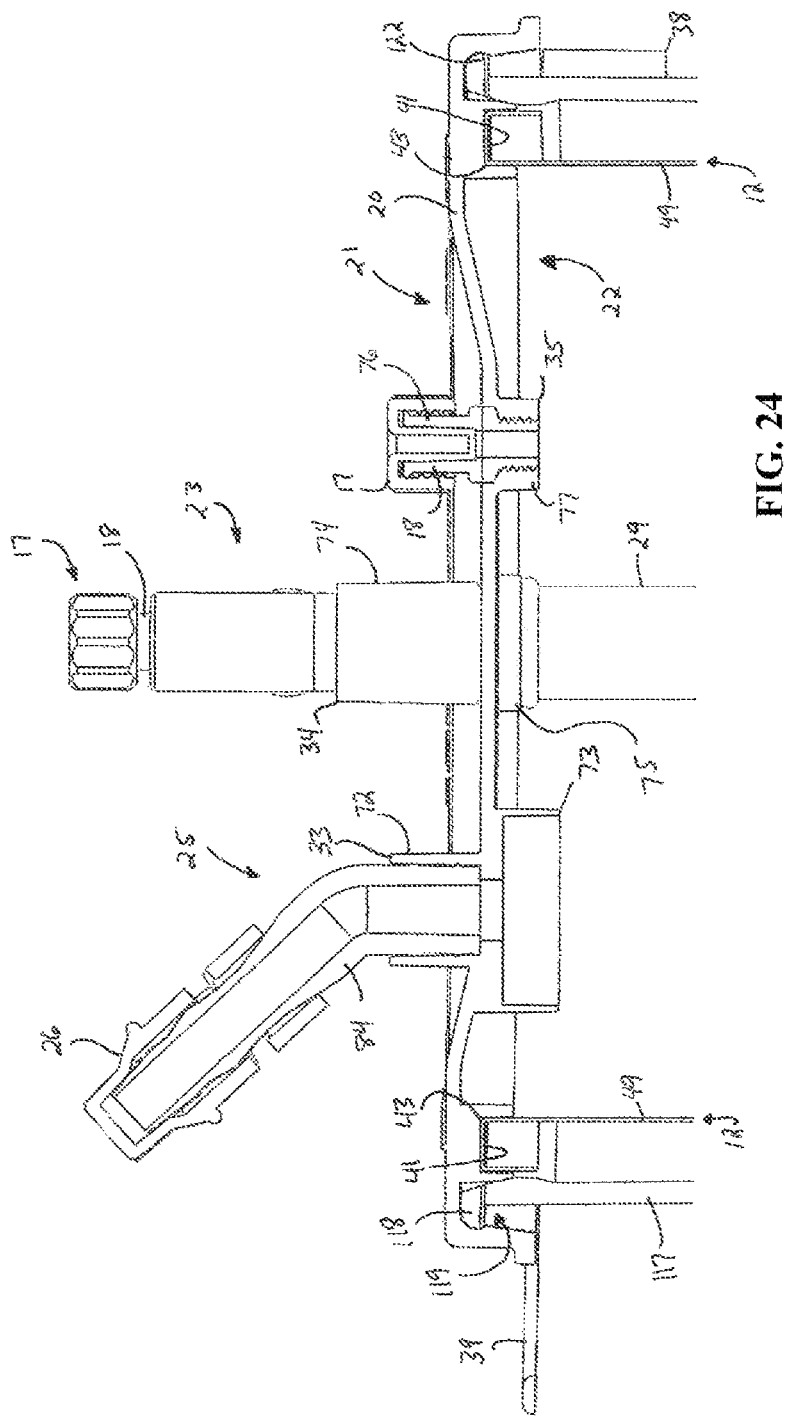
FIG. 24 is a fragmentary longitudinal cross-sectional view through the additive and patient port sites of the first alternative blood collection canister assembly according to the present invention showing a fragmentary upper portion of a hard shell canister and a fragmentary upper portion of a liner assembly attached to the first alternative lid assembly.
Figure 25:
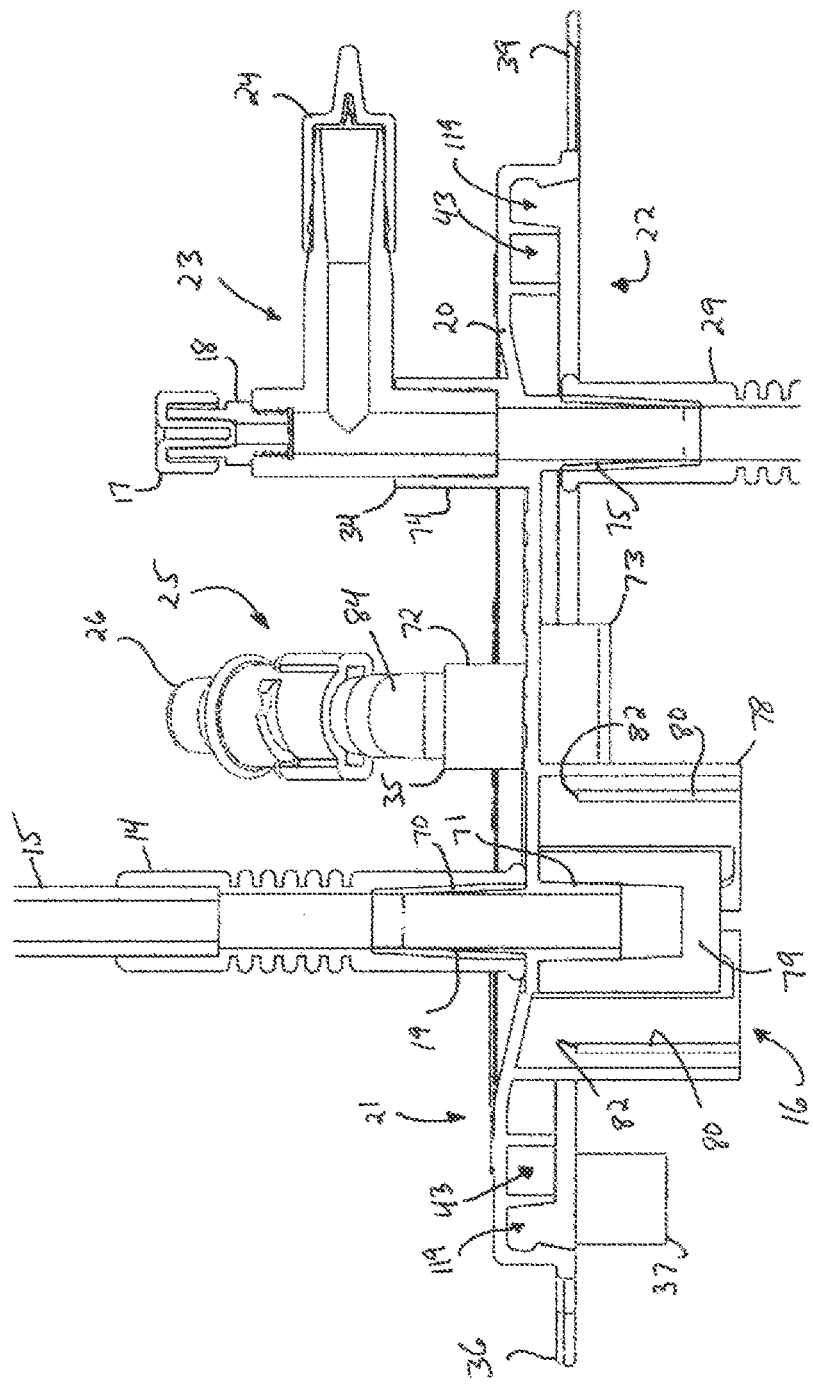
FIG. 25 is a fragmentary longitudinal cross-sectional view through the vacuum and transfer port sites of the first alternative blood collection canister assembly according to the present invention with a fragmentary lower portion of a vacuum tube element attached to the vacuum port and a fragmentary upper portion of a flex connector attached to the transfer port.
Figure 28:
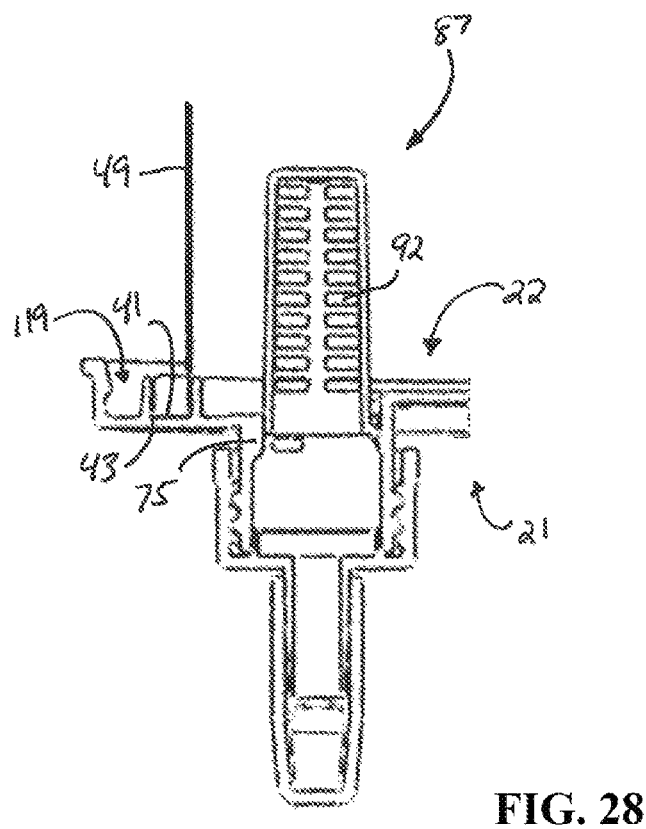
FIG. 28 is an enlarged longitudinal cross-sectional view through the top drain filter assembly of the second alternative blood collection canister assembly according to the present invention.

The dip tube assembly 27 is preferably flexibly connected to the transfer port 34 such that the flexibly connected dip tube assembly 27 and the flexible liner material of the liner assembly 12 enabling collapsibility of the blood collection canister assembly 10 for compact shipping, storage and disposal as generally depicted in FIG. 23.

The blood collection canister assembly according to the present invention may further preferably provide a primary lid portion 20 comprising an inner mouth-receiving groove 43 and an outer mouth-receiving groove 119. The inner mouth-receiving groove 43 receives the upper liner mouth 41 and attaches, via a preferably permanent bond, the primary lid portion 20 to the liner assembly 12. The outer mouth-receiving groove 119 receives an upper canister mouth 118 of a hard shell canister 117 for attaching the hard shell canister 117 to the blood collection canister assembly. Thus, the blood collection canister assembly according to the present invention is optionally usable in combination with the hard shell canister 117.

The patient port 33 may be preferably outfitted with a patient port assembly 25 having a patient port cap 26 and a patient port elbow structure as at 84. The patent port cap 26 is rotatable relative to the patient port elbow structure 84 and thereby cooperable with outer surfacing 86 of the elbow structure 84 for simultaneously maintaining (a) air pressure between liner assembly 12 and hard shell canister 117 and (b) a sterile environment within the combination blood collection canister assembly and hard shell canister 117.

Other optional features include the combination of at least one bio-coated single lumen line; select port(s) (e.g. the patient port 33 and/or the transfer port 34) being outfitted with a Luer lock assembly for generally enhancing functionality of the blood collection canister assembly; and the transfer port 34 may be preferably outfitted with a universal connection point as at 88 for coupling male or female couplings 89 or 90 of external auto-transfusion lines, for example. Accordingly, although the invention has been described by reference to certain preferred and alternative embodiments, it is not intended that the novel arrangements be limited thereby, but that modifications thereof are intended to be included as falling within the broad scope and spirit of the foregoing disclosures, the appended claims and drawings.

What is claimed is:

1. An invertible blood collection canister assembly for (a) collecting and transferring blood in an upright, first configuration via externally imparted force and (b) transferring blood in an inverted, second configuration via gravitational force, the blood collection canister assembly comprising:
   a liner assembly, the liner assembly comprising a flexible liner material defining an inner liner space an upper liner mouth;

a lid assembly, the lid assembly comprising a primary lid portion, the primary lid portion being attachable to the upper liner mouth and comprising a series of ports, the series of ports including a vacuum port, a patient port, and a transfer port, the vacuum port for communicating with a vacuum line and comprising a vacuum filter assembly on an interior side of the lid assembly, the vacuum filter assembly comprising an outer shroud element and an inner vacuum filter element, the vacuum line for directing blood transfer from a patient via the blood collection canister assembly, the patient port for receiving directed blood transfer from the patient, the inner vacuum filter element for absorbing blood and sealing the vacuum port when fully absorbed, the transfer port for transferring collected blood to a separate reservoir for further processing and comprising a blood inlet, the outer shroud element comprising at least one blood-letting slot, each blood-letting slot having an open first end and a terminal slot extent opposite the open first end, each terminal slot extent being differently elevated relative to the blood inlet for maximizing blood drainage from the shroud element when in the inverted, second configuration.

2. The blood collection canister assembly of claim 1 wherein the inner vacuum filter element of the vacuum port, when absorbed with blood, provides a hydrophobic barrier, the hydrophobic barrier for sealing canister contents from the external vacuum source and for preventing overfill of the liner assembly with canister contents.

3. The blood collection canister assembly of claim 1 wherein the vacuum port is outfitted with the vacuum line, the vacuum line being bendable into an arched configuration and connectable to an external vacuum source for providing a gravity-based mechanical barrier against contamination.

4. The blood collection canister assembly of claim 1 comprising a dip tube assembly, the dip tube assembly being connectable to the transfer port and comprising a dip tube element, the dip tube assembly and transfer port together for transferring collected blood via the dip tube element to a separate reservoir for further processing.

5. The blood collection canister assembly of claim 4 wherein the liner assembly comprises a liner bottom and a liner wall orthogonal to the liner bottom, the liner bottom having a radially outer annular depression and a radially inner kick-up, the radially outer annular depression having a liner bottom radius of curvature, the dip tube assembly comprising a transfer filter, the transfer filter having a filter arc length form, a filter upper portion, and a filter bottom portion, the filter arc length form having a filter radius of curvature equal to the liner bottom radius of curvature, the filter bottom portion thus being seatable in the radially outer annular depression in radially outer adjacency to the radially inner kick-up for (a) maintaining the dip tube element in parallel relation to the liner wall and (b) filtering blood collected in the radially outer annular depression and transferable via the dip tube assembly.

6. The blood collection canister assembly of claim 5 wherein the radially outer annular depression comprises an outer diameter, an inner diameter and an arc length segment, the filter bottom spanning the arc length segment intermediate the outer and inner diameters and comprising a planar, inner footprint portion and a radiused outer bottom portion extending outwardly and upwardly from the planar, inner footprint portion, the planar, inner footprint portion and the radiused outer bottom portion each comprising blood intake apertures for inletting blood.

7. The blood collection canister assembly of claim 6 wherein the radially inner kick-up of the liner bottom externally defines a dimple feature, the dimple feature providing an external hollow and comprising an inner dimple diameter at a planar upper dimple portion, a hanger element being externally and hingedly attached to the dimple feature within the external hollow.

8. The blood collection canister assembly of claim 7 wherein the hanger element comprises a hanger diameter cooperable with the inner dimple diameter for enabling a hanger element stowed position within the external hollow in adjacency to the planar upper dimple portion, the dimple feature and hanger element stowed position thus for enhancing functional and stowage characteristics of the blood collection canister assembly.

9. The blood collection canister assembly of claim 6 wherein the blood intake apertures formed in and coplanar with the planar, inner footprint portion define a first aperture shape and the blood intake apertures formed in the radiused outer bottom portion define a second aperture shape.

10. The blood collection canister assembly of claim 4 wherein the dip tube assembly is flexibly connected to the transfer port, the flexibly connected dip tube assembly and the flexible liner material for enabling collapsibility of the blood collection canister assembly for compact shipping, storage and disposal.

11. The blood collection canister assembly of claim 1 wherein the series of ports comprise at least one additive port, the at least one additive port for enabling the user to add material to the inner liner space.

12. The blood collection canister assembly of claim 1 wherein the primary lid portion comprises an inner mouth-receiving groove and an outer mouth-receiving groove, the inner mouth-receiving groove for receiving the upper liner mouth and attaching the primary lid portion to the liner assembly, the outer mouth-receiving groove for receiving an upper canister mouth of a hard shell canister for attaching the hard shell canister to the blood collection canister assembly, the blood collection canister assembly thereby being usable in combination with the hard shell canister.

13. The blood collection canister assembly of claim 12 wherein the patient port is outfitted with a patient port assembly, the patient port assembly comprising a patient port cap and a patient port elbow structure, the patent port cap being rotatable relative to the patient port elbow structure for simultaneously maintaining (a) air pressure between liner assembly and hard shell canister and (b) a sterile environment within the blood collection canister assembly.

14. The blood collection canister assembly of claim 1 usable in combination with at least one bio-coated single lumen line.

15. The blood collection canister assembly of claim 14 wherein that at least one bio-coated single lumen line is capable of being utilized as a suction line via the blood collection canister assembly.

16. The blood collection canister assembly of claim 1 wherein a select port is outfitted with a Luer lock assembly, the select port being selected from the group consisting of the patient port and the transfer port, the Luer lock assembly for enhancing functionality of the blood collection canister assembly.

17. The blood collection canister assembly of claim 1 wherein the transfer port is outfitted with a universal port, the universal port for coupling with male or female couplings.

18. The blood collection canister assembly of claim 17 wherein the universal port comprises an outer tapered surface and an inner tapered surface, the outer and inner tapered surfaces each comprising a tapered slope, the tapered slopes of the outer and inner tapered surfaces being uniformly angled and opposite relative to a central port axis of the universal port.

19. A blood collection canister assembly for collecting and transferring blood in an upright, first configuration via externally imparted force, the blood collection canister assembly comprising:
a liner assembly, the liner assembly comprising a flexible liner material, an upper liner mouth, a liner bottom, and liner wall, the flexible liner material defining an inner liner space, the liner bottom having a radially outer annular depression and a radially inner kick-up, the radially outer annular depression having a liner bottom radius of curvature, the liner wall extending upwardly orthogonally relative to the liner bottom;
a lid assembly, the lid assembly comprising a primary lid portion and a dip tube assembly, the primary lid portion being attachable to the upper liner mouth and comprising a rigid material construction and a series of ports, the series of ports including a vacuum port, a patient port, and a transfer port, the vacuum port for communicating with a vacuum line, the vacuum line for directing blood transfer from a patient via the blood collection canister assembly, the patient port for receiving directed blood transfer from the patient, the dip tube assembly being connectable to the transfer port, the transfer port and dip tube assembly together for transferring collected blood to a separate reservoir for further processing, the dip tube assembly comprising a transfer filter and dip tube element, the transfer filter having a filter arc length form, a filter upper portion, and a filter bottom portion, the filter arc length form having a filter radius of curvature equal to the liner bottom radius of curvature, the filter bottom portion being seatable in the radially outer annular depression in radially outer adjacency to the radially inner kick-up for maintaining the dip tube element in parallel relation to the liner wall and filtering blood collected in the radially outer annular depression and transferable via the dip tube assembly.

20. The blood collection canister assembly of claim 19 wherein the radially outer annular depression comprises an outer diameter, an inner diameter and an arc length segment, the filter bottom spanning the arc length segment intermediate the outer and inner diameters and comprising a planar, inner footprint portion and a radiused outer bottom portion extending outwardly and upwardly from the planar, inner footprint portion, the planar, inner footprint portion and the radiused outer bottom portion each comprising blood intake apertures for inletting blood.

21. The blood collection canister assembly of claim 20 wherein the radially inner kick-up of the liner bottom externally provides a dimple feature, the dimple feature providing an external hollow and comprising an inner dimple diameter at a planar upper dimple portion, a hanger element being externally and hingedly attached to the dimple feature within the external hollow.

22. The blood collection canister assembly of claim 21 wherein the hanger element comprises a hanger diameter cooperable with the inner dimple diameter for enabling a hanger element stowed position within the external hollow in adjacency to the planar upper dimple portion, the dimple feature and hanger element stowed position thus for enhancing functional and stowage characteristics of the blood collection canister assembly.

23. The blood collection canister assembly of claim 20 wherein the blood intake apertures formed in the planar, inner footprint portion define a first aperture shape and the blood intake apertures formed in the radiused outer bottom portion define a second aperture shape.

24. The blood collection canister assembly of claim 19 wherein the dip tube assembly is flexibly connected to the transfer port, the flexibly connected dip tube assembly and the flexible liner material for enabling collapsibility of the blood collection canister assembly for compact shipping, storage and disposal.

25. The blood collection canister assembly of claim 19 wherein the series of ports comprise at least one additive port, the at least one additive port for enabling the user to add material to the inner liner space.

26. The blood collection canister assembly of claim 19 wherein the primary lid portion comprises an inner mouth-receiving groove and an outer mouth-receiving groove, the inner mouth-receiving groove for receiving the upper liner mouth and attaching the primary lid portion to the liner assembly, the outer mouth-receiving groove for receiving an upper canister mouth of a hard shell canister for attaching the hard shell canister to the blood collection canister assembly, the blood collection canister assembly thereby being usable in combination with the hard shell canister.

27. The blood collection canister assembly of claim 26 wherein the patient port is outfitted with a patient port assembly, the patient port assembly comprising a patient port cap and a patient port elbow structure, the patent port cap being rotatable relative to the patient port elbow structure for simultaneously maintaining (a) air pressure between liner assembly and hard shell canister and (b) a sterile environment within the blood collection canister assembly.

28. The blood collection canister assembly of claim 19 usable in combination with at least one bio-coated single lumen line.

29. The blood collection canister assembly of claim 28 wherein that at least one bio-coated single lumen line is capable of being utilized as a suction line via the blood collection canister assembly.

30. The blood collection canister assembly of claim 19 wherein a select port is outfitted with a Luer lock assembly, the select port being selected from the group consisting of the patient port and the transfer port, the Luer lock assembly for enhancing functionality of the blood collection canister assembly.

31. The blood collection canister assembly of claim 19 wherein the transfer port is outfitted with a universal connection point, the universal connection point for coupling with male or female couplings.

32. The blood collection canister assembly of claim 31 wherein the universal port comprises an outer tapered surface and an inner tapered surface, the outer and inner tapered surfaces each comprising a tapered slope, the tapered slopes of the outer and inner tapered surfaces being uniformly angled and opposite relative to a central port axis of the universal port.

33. The blood collection canister assembly of claim 19 wherein the vacuum port is outfitted with the vacuum line, the vacuum line being bendable into an arched configuration and connectable to an external vacuum source for providing a gravity-based mechanical barrier against contamination.

34. The blood collection canister assembly of claim 19 being invertible into a second configuration for transferring blood via gravitational force, the vacuum port comprising a vacuum filter assembly on an interior side of the lid assembly, the vacuum filter assembly comprising a shroud element and a vacuum filter element, the vacuum filter element for absorbing blood and sealing the vacuum port when fully absorbed, the transfer port comprising a blood inlet, the shroud element comprising at least one blood-letting slot, each blood-letting slot having an open first end and a terminal slot extent opposite the open first end, each terminal slot extent being differently elevated relative to the blood inlet for maximizing blood drainage from the shroud element when inverted into the second configuration.

* * * * *